(12) United States Patent
Bocchi et al.

(10) Patent No.: US 9,891,157 B2
(45) Date of Patent: Feb. 13, 2018

(54) MICROANALYSIS OF CELLULAR FUNCTION

(75) Inventors: Massimo Bocchi, Sasso Marconi (IT); Roberto Guerrieri, Bologna (IT)

(73) Assignee: CELLPLY S.R.L., Bologna (IT)

( * ) Notice: Subject to any disclaimer, the term of this patent is extended or adjusted under 35 U.S.C. 154(b) by 1262 days.

(21) Appl. No.: 13/991,378

(22) PCT Filed: Dec. 5, 2011

(86) PCT No.: PCT/EP2011/071819
§ 371 (c)(1),
(2), (4) Date: Jun. 3, 2013

(87) PCT Pub. No.: WO2012/072822
PCT Pub. Date: Jun. 7, 2012

(65) Prior Publication Data
US 2013/0261021 A1    Oct. 3, 2013

Related U.S. Application Data

(60) Provisional application No. 61/419,377, filed on Dec. 3, 2010.

(51) Int. Cl.
*G01N 1/40*     (2006.01)
*G01N 33/50*    (2006.01)
(Continued)

(52) U.S. Cl.
CPC ........ *G01N 15/1404* (2013.01); *B01L 3/5088* (2013.01); *B01L 3/50273* (2013.01);
(Continued)

(58) Field of Classification Search
CPC combination set(s) only.
See application file for complete search history.

(56) References Cited

U.S. PATENT DOCUMENTS 4,747,919 A    5/1988   Anderson
5,496,697 A    3/1996   Parce et al.
(Continued)

FOREIGN PATENT DOCUMENTS

CN    101460253 A    6/2009
EP      1088592 A2   4/2001
(Continued)

OTHER PUBLICATIONS

Bocchi et al. "Dielectrophoretic trapping in microwells for manipulation of single cells and small aggregates of particles" Biosensors and Bioelectronics 24 (2009) 1177-1183.
(Continued)

*Primary Examiner* — Brian R Gordon
(74) *Attorney, Agent, or Firm* — Faegre Baker Daniels LLP

(57) ABSTRACT

An inverted microwell (102) provides rapid and efficient microanalysis system (100) and method for screening of biological particles (128), particularly functional analysis of cells on a single cell basis. The use of an inverted open microwell system (102) permits identification of particles, cells, and biomolecules that may be combined to produce a desired functional effect also functional screening of secreted antibody therapeutic activity as well as the potential to recover cells and fluid, and optionally expand cells, such as antibody secreting cells, within the same microwell.

22 Claims, 16 Drawing Sheets

(51) Int. Cl.

| | |
|---|---|
| *G01N 15/14* | (2006.01) |
| *B01L 3/00* | (2006.01) |
| *B03C 5/00* | (2006.01) |
| *B03C 5/02* | (2006.01) |
| *G01N 27/447* | (2006.01) |
| *C12M 1/32* | (2006.01) |

(52) U.S. Cl.
CPC ........ *B01L 3/502792* (2013.01); *B03C 5/005* (2013.01); *B03C 5/022* (2013.01); *B03C 5/026* (2013.01); *G01N 1/4077* (2013.01); *G01N 15/1484* (2013.01); *G01N 27/44791* (2013.01); *G01N 33/50* (2013.01); *G01N 33/5005* (2013.01); *B01L 2200/0652* (2013.01); *B01L 2300/0645* (2013.01); *B01L 2300/0829* (2013.01); *B01L 2300/0864* (2013.01); *B01L 2400/0424* (2013.01); *B03C 2201/26* (2013.01); *C12M 23/12* (2013.01); *G01N 2015/149* (2013.01); *G01N 2015/1415* (2013.01); *G01N 2015/1481* (2013.01)

(56) References Cited

U.S. PATENT DOCUMENTS

| | | | |
|---|---|---|---|
| 5,846,396 A | | 12/1998 | Zanzucchi et al. |
| 6,932,893 B2 | | 8/2005 | Bech et al. |
| 7,081,189 B2 | | 7/2006 | Squires et al. |
| 7,189,578 B1 | | 3/2007 | Feng et al. |
| 7,238,268 B2 | | 7/2007 | Ramsey et al. |
| 7,776,553 B2 | | 8/2010 | Love et al. |
| 9,039,883 B2 | * | 5/2015 | Guerrieri ................ B03C 5/005 204/547 |
| 2002/0036139 A1 | | 3/2002 | Becker et al. |
| 2002/0053399 A1 | | 5/2002 | Soane et al. |
| 2002/0092767 A1 | | 7/2002 | Bjornson et al. |
| 2002/0125139 A1 | | 9/2002 | Chow et al. |
| 2002/0142482 A1 | * | 10/2002 | Wu ..................... B01L 3/50273 436/177 |
| 2002/0182657 A1 | | 12/2002 | Ranger |
| 2002/0182749 A1 | * | 12/2002 | Singh .................... B01L 3/5025 436/514 |
| 2003/0039585 A1 | * | 2/2003 | Freeman ............... B01L 3/5025 506/32 |
| 2003/0087309 A1 | * | 5/2003 | Chen ..................... B01J 19/0046 435/7.1 |
| 2004/0011652 A1 | | 1/2004 | Bressler |
| 2005/0139473 A1 | | 6/2005 | Washizu et al. |
| 2006/0196772 A1 | | 9/2006 | Kim et al. |
| 2006/0231405 A1 | | 10/2006 | Hughes et al. |
| 2007/0243523 A1 | | 10/2007 | Ionescu-Zanetti et al. |
| 2008/0067068 A1 | | 3/2008 | Li |
| 2008/0210558 A1 | | 9/2008 | Sauter-Starace et al. |
| 2009/0107907 A1 | | 4/2009 | Chen et al. |
| 2009/0258383 A1 | | 10/2009 | Kovac et al. |
| 2009/0288963 A1 | * | 11/2009 | Guerrieri ................ B03C 5/005 205/792 |
| 2010/0152054 A1 | | 6/2010 | Love et al. |
| 2012/0034623 A1 | * | 2/2012 | Hulsken ............... G01N 1/4005 435/7.2 |
| 2013/0068618 A1 | | 3/2013 | Harrer et al. |
| 2013/0134040 A1 | | 5/2013 | Lee et al. |
| 2013/0252258 A1 | | 9/2013 | Bocchi et al. |
| 2013/0256137 A1 | | 10/2013 | Holt |
| 2013/0261021 A1 | | 10/2013 | Bocchi et al. |

FOREIGN PATENT DOCUMENTS

| | | |
|---|---|---|
| WO | WO199962622 A1 | 9/1999 |
| WO | WO2001009297 A1 | 2/2001 |
| WO | WO2007138464 A2 | 12/2007 |
| WO | WO2009151505 A1 | 12/2009 |
| WO | 2010085275 A1 | 7/2010 |
| WO | WO2012072822 A1 | 6/2012 |
| WO | WO2012072823 A1 | 6/2012 |

OTHER PUBLICATIONS

Bocchi et al. "Inverted open microwells for analysis and functional sorting of single live cells" 15th International Conference on Miniaturized Systems for Chemistry and Life Sciences Oct. 2-6, 2011, Seattle, Washington, USA.

Bocchi et al. "Inverted open microwells for cell trapping, cell aggregate formation and parallel recovery of live cells" Lab Chip, 2012, 12, 3168-3176.

Dura et al. "Spatially and temporally controlled immune cell interactions using microscale tools" Current Opinion in Immunology 2015, 35:23-29.

Faenza et al. "Impedance measurement technique for high-sensitivity cell detection in microstructures with non-uniform conductivity distribution" Lab Chip, 2012, 12, 2046-2052.

Konry et al. "Droplet-based microfluidic platforms for single T cell secretion analysis of IL-10 cytokine" Biosens Bioelectron. Jan. 15, 2011; 26(5): 2707-2710. Published online Sep. 15, 2010 doi:10.1016/j.bios.2010.09.006).

International Search Report and Written Opinion issued in PCT/EP2011/071820, dated Mar. 30, 2012, 11 pages.

"Apoptosis, Cell Death, and Cell Proliferation—3rd Edition," Roche Applied Science, 174pp (NPL uploaded in 5 parts).

Bessette, Paul H., et al., "Microfluidic Library Screening for Mapping Antibody Epitopes," Analytical Chemistry, vol. 79, No. 5, Mar. 1, 2007, pp. 2174-2178, XP55022596.

Bhat, Rauf et al., "Serial Killing of Tumor Cells by Human Natural Killer Cells—Enhancement by Therapeutic Antibodies", PLOS ONE, vol. 2, No. 3, 2007, e326, 7 pages.

Bocchi, Massimo et al., "Electronic Microsystems for Handling of Rare Cells," IEEE Transactions on Electron Devices, vol. 57, No. 1, Jan. 1, 2010, pp. 244-255.

Duqi, E. et al., "Automated isolation of a programmable number of cells into microwells using DEP forces and optical detection", International Conference on Microtechnologies in Medicine and Biology, May 2011, 2 pages.

Faenza, A. et al., "Controlled isolation and patterning of K562 leukemia cells using electrically activated microchannels", International Conference on Microtechnologies in Medicine and Biology, May 2011.

Faenza, Andrea et al., "Continuous Impedance Monitoring of Single Cells Delivered in Open Microwell Arrays", presented at the 13th International Conference on Miniaturized Systems for Chemistry and Life Sciences, Nov. 1-5, 2009, Jeju, Korea, 3 pages.

Han et al., "Integration of single oocyte trapping, in vitro fertilization and embryo culture in a microwell-structured microfluidic device", Lab on a Chip, vol. 10, No. 21, 2010, pp. 2848-2854.

International Search Report and Written Opinion issued in PCT/EP2011/071819, dated May 4, 2012, 14 pages.

Jin, Aishun et al., "A rapid and efficient single-cell manipulation method for screening antigen-specific antibody-secreting cells from human peripheral blood" Nature Medicine, vol. 15, 2009, pp. 1088-1092.

Lucas, et al. "Lab-on-a-chip Immunoassay for Multiple Antibodies Using Microsphere Light Scattering and Quantum Dot Emission," Biosensors and Bioelectronics, Elsevier BV, NL, vol. 23, No. 5, Nov. 15, 2007, pp. 675-681, XP022345923.

Neri, Simona et al., "Calcein-Acetyoxymethyl Cytotoxicity Assay: Standardization of a Method Allowing Additional Analyses on Recovered Effector Cells and Supermatants", Clinical and Diagnostic Laboratory Immunology, Nov. 2011, vol. 8, No. 6 pp. 1131-1135.

Rastogi, Vinayak, et al., "Development and Evaluation of Realistic Microbiosassays in Freely Suspended Dropletson a Chip," Biomicrofluids, AIP, US, Online, vol. 1, No. 1, Mar. 1, 2007, pp. 14107-1, XP008149939.

(56) References Cited

OTHER PUBLICATIONS

Ronan, J.L. et al., "Optimization of the surfaces used to capture antibodies from single hybridomas reduces the time required for microengraving" J. Immunol. Methods, vol. 340, No. 2, Jan. 2009, pp. 164-169.

* cited by examiner

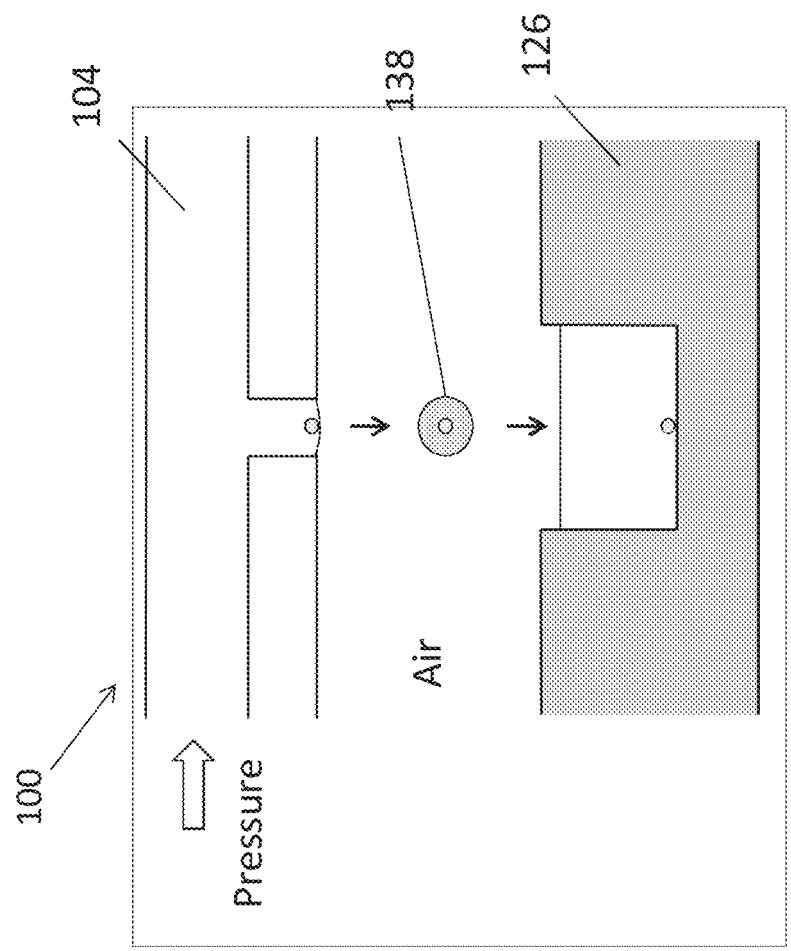

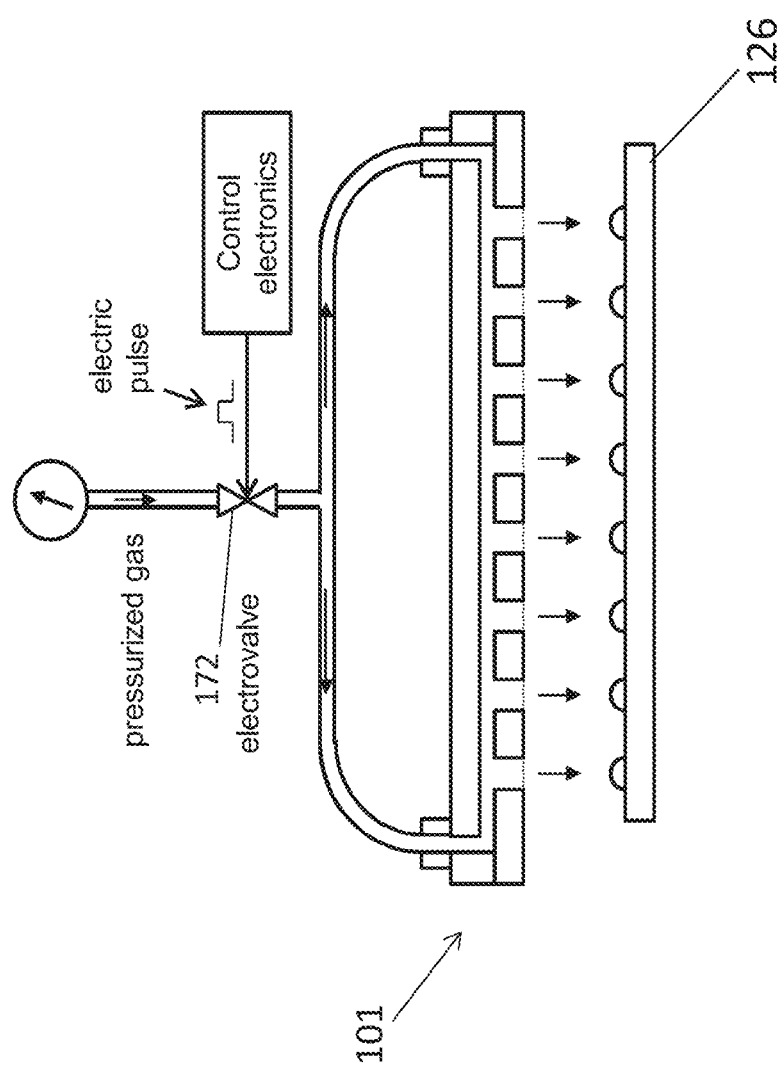

MICROANALYSIS OF CELLULAR FUNCTION

CROSS-REFERENCE TO RELATED APPLICATIONS

This application is a Continuation of U.S. application Ser. No. 13/991,378, entitled "Microanalysis of Cellular Function", filed Jun. 3, 2013, which is a U.S. national phase application, filed pursuant to 35 U.S.C. §371, of PCT application No. PCT/EP2011/071819, entitled "Microanalysis of Cellular Function," filed Dec. 5, 2011, which claims the benefit of U.S. Provisional Application No. 61/419,377, entitled "Microanalysis of Cellular Function", filed Dec. 3, 2010, which are herein incorporated by reference in their entireties for all purposes.

BACKGROUND OF THE INVENTION

Systems for high throughput and efficient analysis of biological particles, including single live cells, are needed to enable rapid and valuable identification of particles, including cells, molecules, and the like, that possess desired functions, for example that produce or induce a desired biological outcome. Such systems are needed for drug discovery, diagnosis, screening of candidate molecules, and the like. In a preferred system, the particle is retained in a viable form and is not damaged significantly by the analytical process.

Current systems that evaluate single particles generally utilize dielectrophoresis (DEP) to manipulate the particles. The electric field imposed upon particles such as cells to levitate and maintain the particle's position during induced reactions and analysis can harm the viability and disrupt the ability of the particle to properly function. Under prolonged use, for example, such damage can lead to lysis and/or cell death. The attachment of particles to a substrate, electrode, or wall of a chamber can also require lysis of the cell to remove it from the system after analysis or to capture cellular products.

It would be very useful to provide a rapid, high throughput system for effectively and efficiently capturing, identifying, and analyzing biological function of single particles, where the particles are not significantly damaged by the system.

SUMMARY OF THE INVENTION

An inverted open microwell system, device and methods of use are disclosed herein that provide rapid and efficient screening and sorting of particles, and particularly of single particles, including single cells. Such screening includes analysis of particular particle characteristics as well as functional properties of the particle that can indicate if a particle or reagent may be therapeutically useful. For example, the characteristics of the particle can include: presence and relative amount of specific binding and/or affinity for ligands, such as cancer cell target antigens; cell to cell binding reactions and interactions, for example lysis, toxicity, biomarker production, electroporation, and the like; induced cellular response and/or reactions, for example, induced by other cells, drugs, compounds, proteins, antibodies, molecules, enzymes, nucleic acid molecules, cell secretions, and the like; induced production of cellular products, for example lytic enzymes, antibodies, biomarkers, and the like. The analysis of these characteristics followed by particle recovery supports methods for functional cell sorting which lead to the isolation of cells or their byproducts, such as secreted molecules, having a proved function and utility, for example, therapeutic utility.

In an embodiment, the single cell analysis can include a plurality of tests, in substantially one reaction scheme or sequentially, for example, with the results of one test providing information for the particular test to follow. For example, a cell known to be associated with a specific disease, for example, a cell obtained from an individual suffering from the disease, can be analyzed in the system for the presence of a particular biomarker, for example, an antigen, expressed protein, or disease characteristic. After preliminary analysis to identify if the single cell demonstrates the biomarker, the same identified cell can be analyzed again for its response to a candidate therapeutic drug, compound, or other cellular treatment expected to be effective to induce a desired response in cells exhibiting the screened biomarker.

Analysis in the inverted open microwell can be accomplished on a single particle, including a single cell, with rapid and efficient timing, and without the need to isolate the particles or products of the particles from complex mixtures. Screening methods include screening of a single cell for functional properties, with the option of recovering an original cell in substantially viable form, for continued analysis, immortalization, and/or clonal expansion identified as having a useful property. Cellular components such as DNA, RNA, proteins, and the like, can also be isolated from the original cell.

The methods permit the identification of desirable particle reactions and interactions early in the development process. An early understanding of cellular function enables final development of useful biological materials with a better understanding of the material's potential for success, and can reduce the number of potential candidates earlier in the development process. Methods for multiple and rapid analyses can be performed on the same particle, for example on a single cell, permitting more rapid advancement in the discovery process.

Precise delivery or exclusion of single cells to microwells, and precise manipulation of cells and other particles in the microchannel and in a specific microwell, delivery of reagents, buffers, markers and the like, including other cells for cell-cell interactions, is facilitated by the inverted open microwell system described herein. Single cells can be evaluated for multiple characteristics, retaining vitality in the open microwell for optional continued testing, immortalization, expansion, and the like. Recovery of the particles, including recovery of the original single cell is possible in a short time frame, using minimal reactants, and recovering cells and products in a substantially viable and useful condition. In particular, deposition of one or more particles, including live cells at the fluid/air interface of an open microwell permits precise particle to particle interactions that can be efficiently monitored and rapidly screened to identify candidate particles, for example cells, for continued analysis and/or clonal expansion in the microwell.

Surprisingly, fluid filling the inverted open microwell 102 having a lower end 108 open to air, is retained without leakage from the open lower end when proper geometrical constraints and fluidic conditions are used. Moreover, the deposited particle(s) 128 are surprisingly retained at the meniscus 122 during fluid washes, placement of additional particles in close proximity of the first, and analytical procedures. The open microwell acts as a "mini-centrifuge" permitting delivery of reagents to the deposited particle(s) for rapid analysis, washes, and continued analysis of the deposited particle without loss. Cells within the microwell retain good viability, for example, after analysis and when recovered from the microwell. Recovery from the microwells can be, for example, onto substrates such as microtiter plates, for example for immortalization and/or expansion. In an embodiment, selected single cells can be incubated and expanded within the microwell.

The invention provides methods and structures implementing an inverted open microwell system that comprises a microwell open at an upper end to a microchannel. In an embodiment, the microwell can be closed at a lower end, preferably with a clear material such as glass or clear polymer to permit viewing of the contents of the microwell. In another embodiment the microwell is open at a lower end to the atmosphere outside the device, for example, air or other gas.

Delivery of one or more particle to a microwell can be by sedimentation, for example, controlled by cell density, fluid speed, loading time, and optionally dielectrophoretic forces. Dielectrophoretic forces can be generated by electrodes connected to proper alternate voltages and positioned in a microchannel, the microchannel positioned over the microwell which is open and in fluid communication with the microchannel. Also provided are methods for efficient particle focusing and interactions, controlled, for example, by electrodes embedded within the open microwell to create dielectrophoretic forces able to manipulate particles, such as single cells, to a desired position within the microwell. Such methods provide a high throughput analytical system using minimal reagents and permitting high-throughput recovery of viable particles post-analysis, including cells and cell products.

The invention further provides methods and structures for guiding and sorting particles, including cells and non-cell particles, with precision, in order to deliver a particle efficiently to a microwell of the inverted open microwell system. Specific embodiments include disposition of electrodes and electrode pairs in the microchannel to enable particle movement with little or no harm to the vitality of the biological materials, such as cells; disposition of electrodes and electrode pairs in the microchannel and in proximity to the microwell, structures that permit controlled access of desired particles to the microwell and that effectively close the microwell and repel unwanted particles; and a pattern of electrodes and electrode pairs within the microwell for detecting and optionally controlling the position of a particle as it passes into and through the microwell, for example, for deposition on the fluid meniscus.

The inverted open microwell system includes one (FIG. 1) or a plurality (FIG. 3) of microwells, where each microwell is in fluid communication with one or with a plurality of microchannels for fluid and particle delivery to the microwell(s). The microchannel is generally disposed above the microwell, the microwell being open to the fluid microchannel at an upper end 106 of the microwell and open at a lower end 108 to the atmosphere outside the device, for example air or other gas, whose properties such as gas composition, humidity, temperature, and absence of contaminants can be controlled. The microwell has a vertical axis 110, for example a central vertical axis, extending between the upper end 106 and the lower end 108 of the microwell 102.

In an embodiment, the vertical wall 112 of the microwell 102 is formed at least in part by a dielectric material 114. The vertical wall may also be formed at least in part by one or more electrodes integrated with a dielectric material, for example, in a laminate configuration that is perpendicular to the vertical axis of the well, the laminate forming the microwell, for example as shown in FIG. 2.

A fluid inserted in the microchannel 104 fills the microwell 102 by capillary action, while surface tension holds the fluid within the open microwell, forming a meniscus 122 at the lower open end 108 of the microwell at the air-fluid interface. The surface of the microchannel and of the microwell can be coated with opposing hydrophilic or hydrophobic materials. For example, the microwell can have a hydrophilic coating and the surface of the microchannel near the open end of the microwell has a hydrophobic coating, or vice versa.

In general, movement of particles within the microchannel and placement of a particle in a particular microwell is accomplished by limiting dilution, sedimentation, electromagnetic forces, gravity, and a combination of these. In one embodiment, controlled manipulation of particles in the inverted open microwell system includes powering of one or more of an array of electrodes suitably positioned in a microwell as well as those electrodes suitably placed in the microchannels. Examples of electrode arrangements are shown in FIGS. 2 and 9-13.

Methods disclosed herein include methods for screening single cells or small groups of cells, including precise aggregates of specific particles. Analysis of single cells is generally provided to identify cells capable of producing a specific response, for example to an added biomaterial that may be a different cell, cell portion, protein, nucleic acid molecule, drug, antibody, enzyme, and the like. The production of precise aggregates permits precised alignment of cells that may together induce a desired response and/or only together can be analyzed for a specific characteristic, ability, or function. The system makes possible, for example, alignment of multiple particles in an aggregate, the cells being in direct contact or in close proximity for functional contact. Such alignment of cells in a precise aggregate permits rapid and efficient testing of particle-to-particle interactions.

BRIEF DESCRIPTION OF THE FIGURES

FIG. 4 is a diagram showing recovery of microwell contents to a microtiter plate.

FIG. 5 is a diagram showing recovery of microwell contents from a system comprising a plurality of open microwells to a recovery substrate.

FIG. 8A=day 0; FIG. 8B=3 days; FIG. 8C=5 days.

DETAILED DESCRIPTION OF THE PREFERRED EMBODIMENTS

A. Definitions

Figure 1:
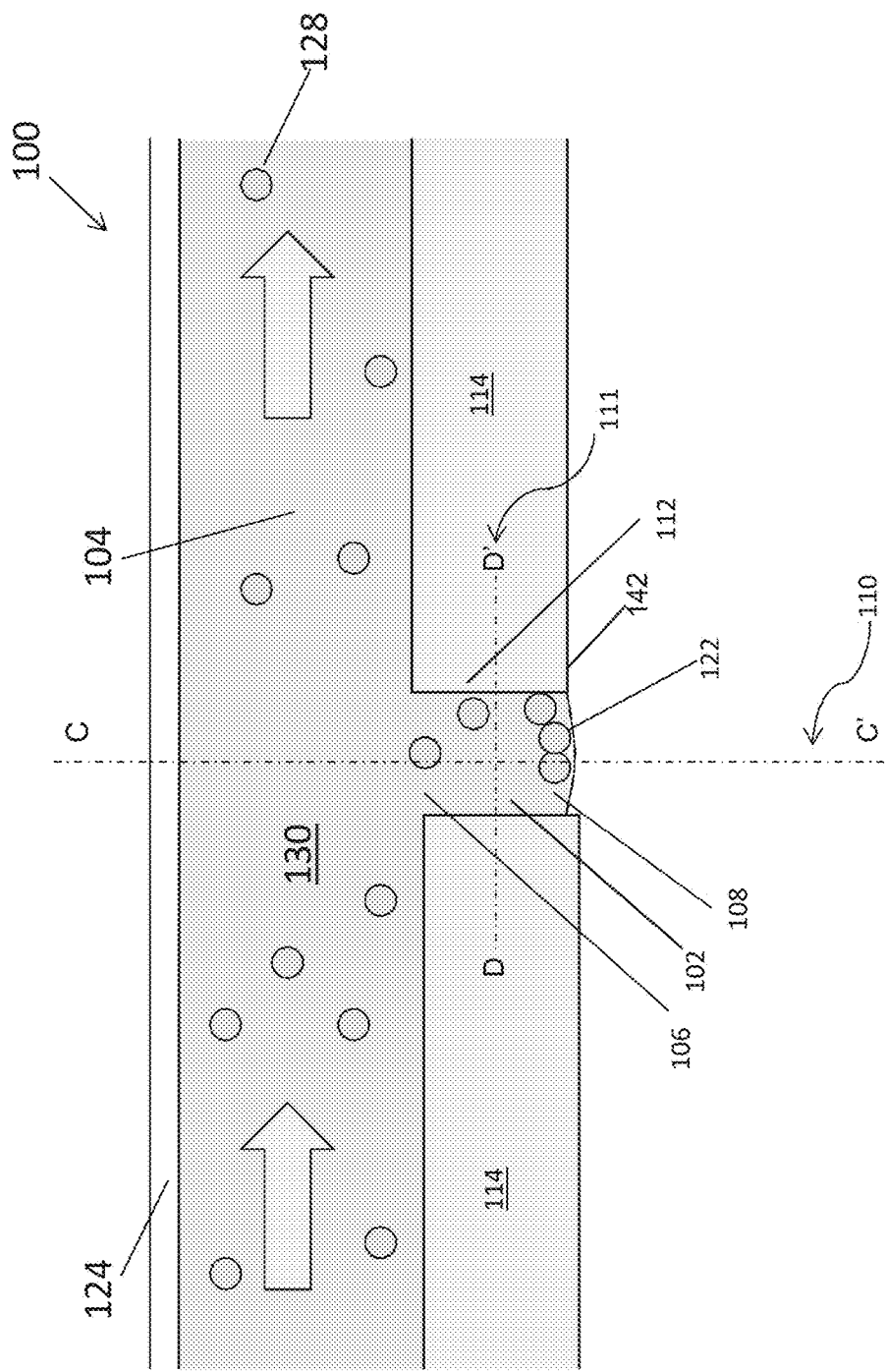
FIG. 1 is a schematic diagram of an inverted open microwell system, showing cells deposited at the meniscus of the open microwell with fluid moving in the microchannel, with particle delivery from the microchannel into the microwell by gravity.

The following terms and phrases are intended to have the definitions shown below:

Microwell, as used herein, means a well formed with micrometer dimensions (less than 1000 micrometers), including height, cross-sectional area, for example, diameter where the microwell is tubular; and volume.

Microchannel, as used herein, means a channel providing fluid to the microwell, having a cross-sectional area of micrometer dimensions (less than 1000 micrometers).

Particle, as used herein, is meant to include any particle that may be delivered, manipulated, reacted, or analyzed in the microwell of the disclosed inverted open microwell system. The particle may be a cell or cellular portion, a microorganism, a biological molecule such as a protein, polynucleotide, antibody, enzyme, or a substrate such as a polymeric particle that may be coated with a reactive substance, for example, an antigen coated sphere, and the like.

Meniscus, as used herein, means the air/fluid interface formed at the lower end of the inverted open microwell by surface tension.

Electrode, as used herein, is an electrical conducting material, for example, metal, such as gold, copper, nickel-gold, and the like. Preferred electrodes are formed of high purity gold.

Dielectric material, as used herein, is an electrical insulating substrate. Preferred dielectric materials for use in the inverted open microwell system include polyimide, such as Kapton® and Pyralux®, Dielectrophoresis, as used herein, is a force exerted on a particle when subjected to a non-uniform electric field.

"A" means at least one.

"Plurality" means two or more.

"Micro" means having at least one dimension less than 1000 micrometers.

"Comprises" or "comprising" means including at least the recited elements or steps, and open to the inclusion of additional elements or steps.

B. Abbreviations

The following abbreviations are used as shown below:
DEP means dielectrophoresis
ASC means antibody secreting cell
CTL means cytotoxic lymphocyte
NK means natural killer cell
LCL means lymphoblastoid cell line
ADCC means antibody-dependent cell cytotoxicity
CMC means complement mediated cytotoxicity
PCB means printed circuit board C. Inverted Open Microwell System and Device The inverted open microwell system includes a device (100) comprising one (FIG. 1) or a plurality (FIG. 3) of microwells, where each microwell (102) is in fluid communication with one or with a plurality of microchannels (104) for fluid and particle delivery to the microwells. The microchannel is generally disposed above the microwell, the microwell being open to the fluid microchannel at an upper end (106) and open at a lower end (108) to the atmosphere outside the device, for example air or other gas. The microwell has a vertical axis (110), for example a central axis, extending between the upper end and the lower end of the microwell. Fluid inserted in the microchannel fills the microwell by capillary action, while surface tension holds the fluid within the open microwell, forming a meniscus (122) at the air/fluid interface.

In this application, the atmosphere outside the device at the open lower end of the microwell is exemplified as "air". It is to be understood that the atmosphere may be controlled, for example, in a chamber, to contain gas other than air, for example, enriched with carbon dioxide, nitrogen, or other gas as desired for the maintenance of the particles and/or analysis to be performed within the microwell. The chamber may include a system to control gas composition, humidity, temperature, pressure, and/or other physical parameters and/or to maintain the environment in a sterile condition.

In one embodiment, a closed chamber is created by placing the device substrate 114 upon a microtiter plate whose wells are aligned to the inverted open microwells. The alignment retains space between the open microwell and the surface of the microtiter plate such that the contents of the open microwell and the microtiter plate, for example, fluid contents, are separated. The microtiter wells may contain a liquid medium, for example, a physiological medium used for cell recovery and cell culture, for example, to accept contents of the open microwell when released. The microtiter wells can contain a different medium, such as water or other fluid, for example, to increase the humidity of the closed chamber, Increasing the humidity of the atmosphere of the closed chamber due to evaporation of liquid in the microtiter well, can saturate vapor pressure in the chamber and prevent evaporation of fluid from the inverted open microwell in the chamber. In an embodiment, the atmosphere of the closed chamber is fully saturated, for example, at or about 100% humidity, to prevent evaporation at the meniscus. The temperature of the substrate 114 can be maintained higher than the temperature of the humid air contained in the chamber in order to prevent condensation on the surface of the substrate.

The inverted open microwell system can be used to achieve controlled delivery of one or more particle, such as one or more living cell, to the microwell, to cause interaction of a delivered particle in the microwell with one or more additional particle delivered to the microwell, and/or to permit high-throughput analysis of a biological function, for example, by inducing specific reactions within the microwell, analyzing the results of the reactions, with identification and optional recovery of selected particles and/or biological products of selected particles.

The system can serve as a "mini-centrifuge", with changes in the fluid contained in the channel providing washing and reagent changes within the open microwell without displacement or loss of particle(s) positioned on the meniscus. In one particular embodiment, the fluid contained in the microwell is suitable for dielectrophoretic manipulation of particles. Once a particle is positioned in the microwell, for example on the meniscus, the fluid dielectrophoretic medium can be washed from the microwell and replaced with a suitable assay medium or with a medium suitable for growth and expansion of the positioned particle.

The inverted microwell system provides efficient and effective real-time monitoring of particle functions, including interactions of multiple particles, functional screening, and sorting of particles, for example live cells. In a particular embodiment, the system provides high throughput functional analysis and rapid identification and selection of antibody secreting cells and high affinity antibodies, analysis of lytic activity and selection of desired cytotoxic lymphocytes and natural killer cells, for example by ADCC or CMC assay. The system permits rapid analysis of affinity and specificity of molecules secreted by single cells, for example, monoclonal antibodies, as well as recovery of identified antibody secreting cells and/or secreted antibodies, and also permits expansion of identified cells within the microwell.

Structural attributes of the device, including relative geometries, coatings, pressures, materials, and qualities of the intended fluids, particles, and reagents to be placed in the microwell are optimized for particular analyses to provide optimal functionality. For example, a coating applied to the interior walls of the microwell versus that applied to the walls of the microchannel adjacent to the microwell can be designed to have an opposing hydrophobic/hydrophilic character to repel unwanted materials away from the well and/or to accommodate entry of a desired particle(s).

The diameter and/or length of the microwell is designed to permit the formation of a meniscus at the lower end of the microwell at the interface of the fluid with the outside environment, for example, air, and to permit a particle or particles deposited on the meniscus to be retained with little or no leakage of fluid from the microwell, and to permit exchange of fluids and reagents in the microwell while retaining particle(s) positioned at the meniscus. The width, height and length of the microchannel are designed to create a hydraulic resistance which, under specific fluid flows, produces a pressure in the microchannel within a range which allows the microwells to be filled while preventing the fluid to leak from the bottom side of the microwell. These and other features of the inverted open microwell system and use are described and exemplified herein.

1. Microwell

As shown, for example in FIG. 1, the inverted open microwell device 100 includes a microwell 102 having dimensions in the micrometer range. The open microwell can have a tubular shape, for example with a circular cross-sectional axis. Other shaped microwells can also be used, for example, conical, rectangular, or other geometric shape. In one embodiment the microwell is formed with an expanded width at the upper end extending from a narrowed lower end.

FIG. 1 shows a cross-sectional view of a device 100 including an open microwell 102. The device 100 includes a substrate 114 defining a vertical wall 112 of the microwell 102 that extends transversely between an upper open end 106 to a lower open end 108 of the open microwell 102.

The substrate 114 can be a moldable plastic, for example, poly(methyl methacrylate) (PMMA), polycarbonate, polyethylene naphthalate (PEN), polyethylene terephthalate (PET), cyclo-olefin polymer, and the like.

The substrate 114 may have a thickness, for example, of from about 10 μm to about 500 μm, inclusive, and may be for example, 12.5, 25, or 50 μm in thickness. In some embodiments, particularly these embodiments comprising electrodes, the substrate 114 is formed, at least in part, of a dielectric material, for example, polyimide, Kapton®, Pyralux®, and the like materials.

2. Electrodes

Figure 2:
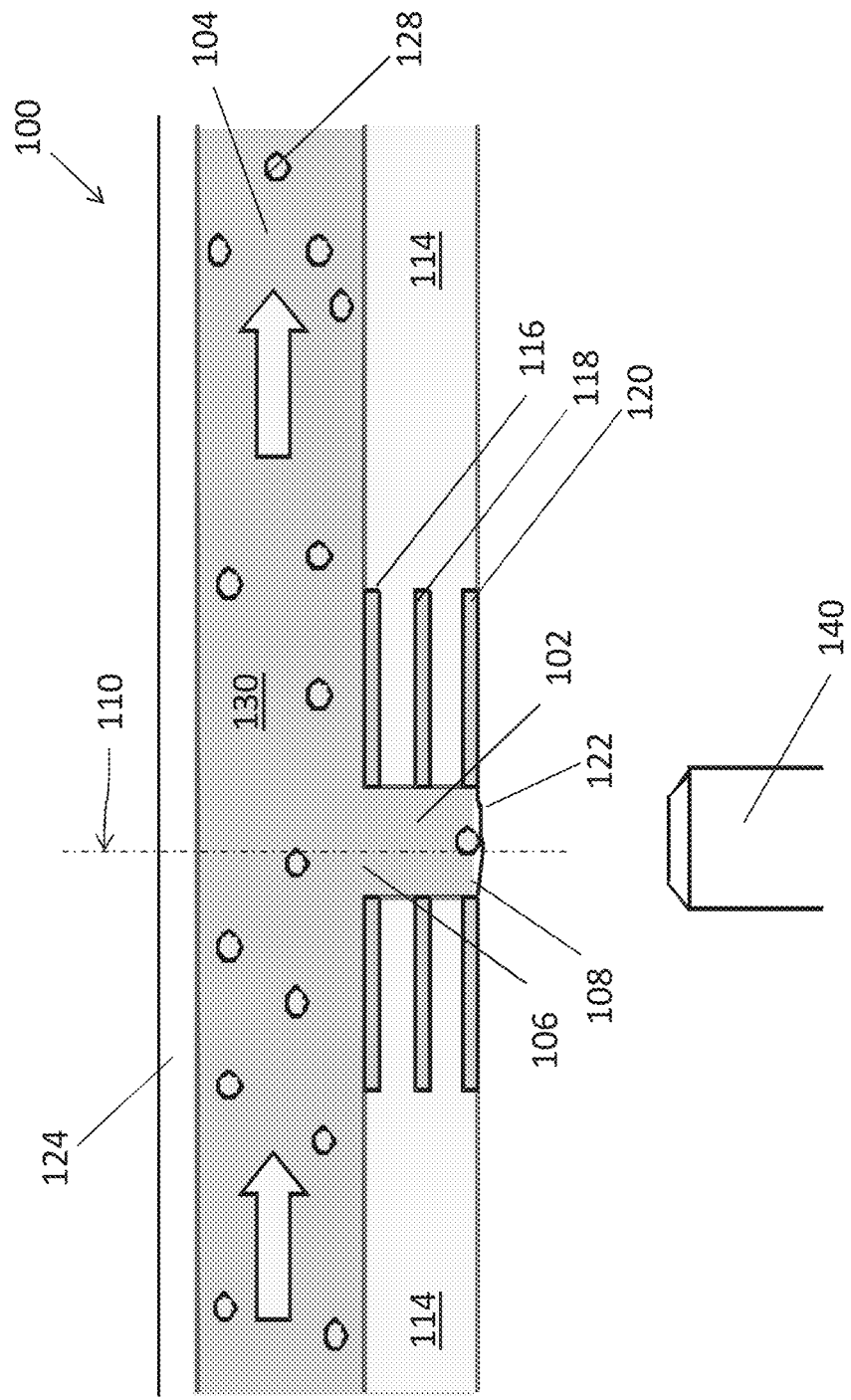
FIG. 2 is a cross sectional diagram showing a 3 electrode configuration in an inverted open microwell system.

As shown in FIG. 2, the inverted microwell system can include one or a plurality of electrodes coupled to a power source for applying voltages to the electrodes. In various embodiments, electrodes can be arranged in the microwell and in the microchannel to control electrical forces on a particle, for example, to push or pull a particle in a microchannel toward and/or into or out of a microwell, or to facilitate a particle's transport from entering the open microwell to the lower end of the microwell, or any portion of these.

While three electrodes 116, 118, 120 are shown in the microwell of in FIG. 2, the device 100 may alternatively include more or fewer electrodes. In an embodiment, the microwell is surrounded by at least one annular electrode 116. In another embodiment, a pair of facing electrodes 116, 116A rings the microwell. In an embodiment, a pair of facing electrodes can be positioned near the upper end 106 of the open microwell, providing controlled entry of a particle 128 to the microwell and/or controlled positioning of a particle along a vertical axis 110, for example a central vertical axis.

Figure 10:
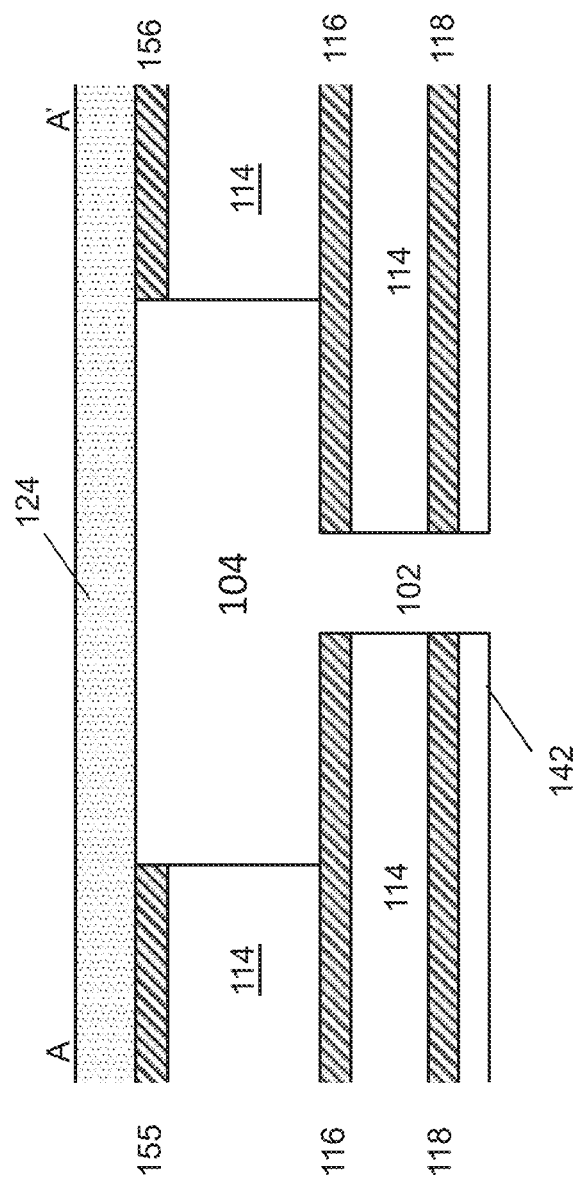
FIG. 10 is a sectional view of the schematic drawing of FIG. 9 through line A-A', showing an arrangement of electrodes in the microwell and microchannel.
Figure 11:
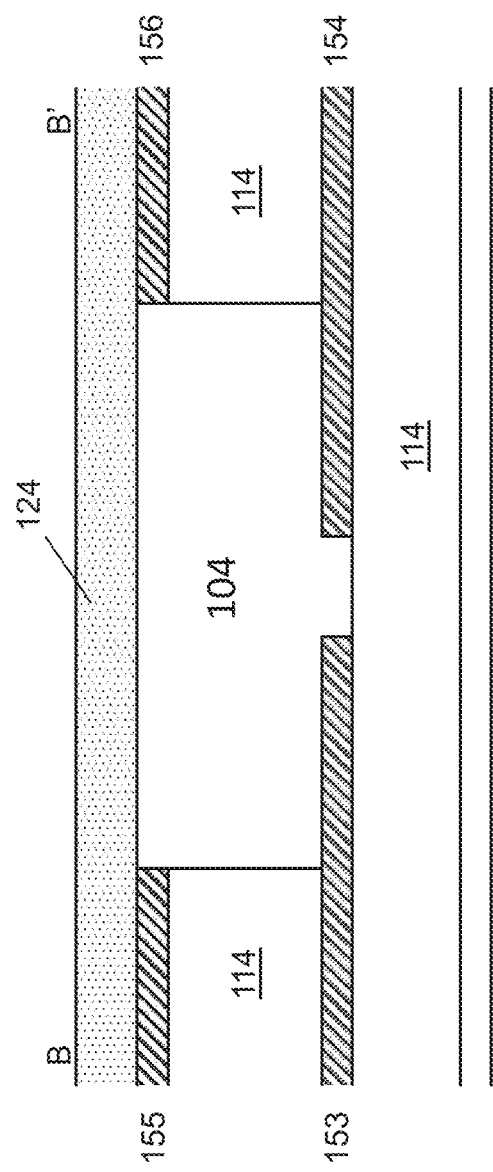
FIG. 11 is a sectional view of the schematic drawing of FIG. 9 through line B-B', showing an arrangement of electrodes in the microchannel.
Figure 12:
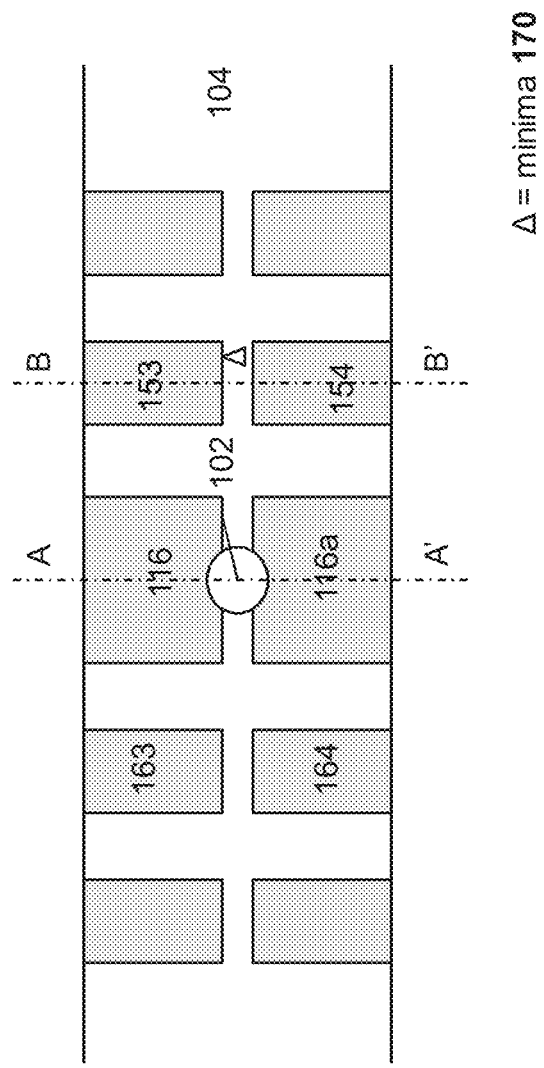
FIG. 12 shows an electrode array centered at the location of a microwell shown through the top of an inverted open microwell system and demonstrating arrangement of electrodes in the microchannel for trapping a particle in the channel at a minimum electrical potential (Δ). This arrangement is most suitable when a fluid flow does not flow in the channel.
Figure 13:
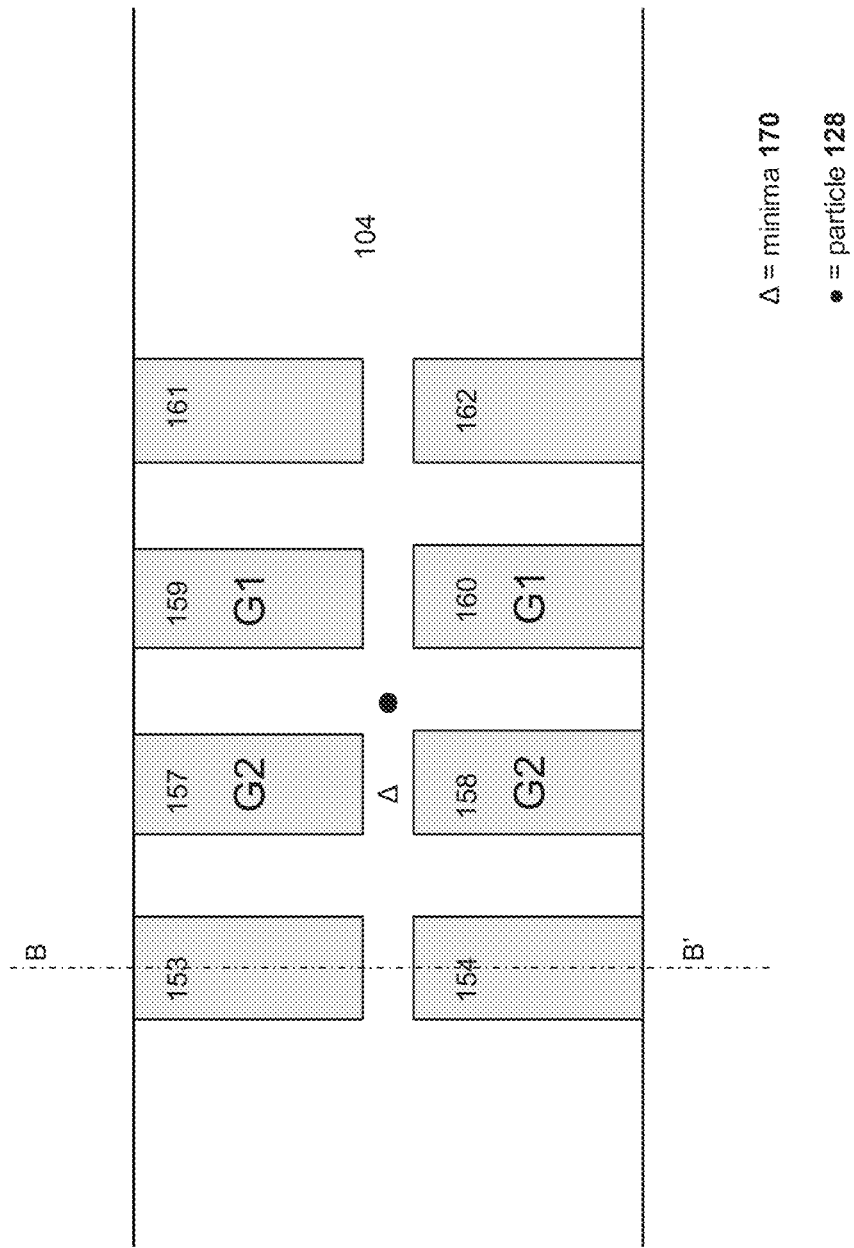
FIG. 13 shows an electrode array centered upstream of a microwell, shown through the top of an inverted open microwell system, and demonstrating arrangement of electrodes in the microchannel for manipulating a particle (●) toward a minimum electrical potential (Δ) established by the specific forces applied by the electrodes.

Electrodes can also be arranged in the microchannel to impact transport of particles. For example, FIGS. 10-11 show possible arrangements of electrodes within the microchannel 155, 156, 153, 154 and within the microwell 116, 118. FIGS. 12-13 demonstrate an exemplary array of electrodes 153-164 disposed in pairs along the microchannel facilitating transport of a particle toward the microwell 102 and away from the microwell 102.

The electrodes are formed of a conductive material that may be, for example, in the form of conductive sheets or plates. In some embodiments, the conductive material comprises a biocompatible metal, such as gold, carbon, or aluminum. In the embodiment shown, the electrodes 116, 118, 120 and 153-164 are embedded in a substrate 114 such that adjacent electrodes are separated from each other by portions of the substrate 114, for example, in a laminate configuration that is perpendicular to the vertical axis 110 of the microwell (see FIG. 2).

3. Microchannel

Figure 3:
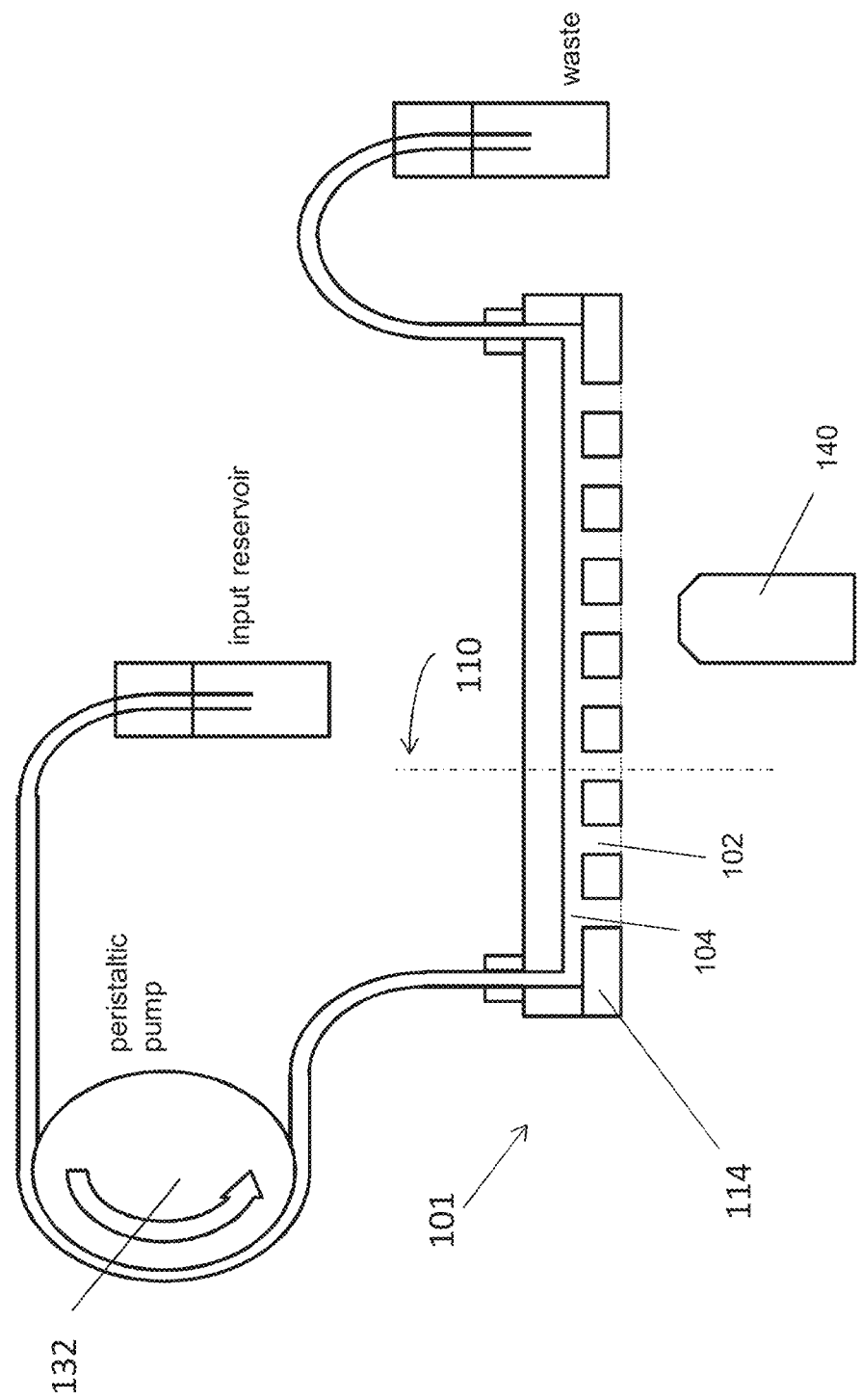
FIG. 3 is a schematic diagram showing an inverted open microwell system comprising a plurality of microwells connected to a fluidic system providing fluids to the microchannels and an imaging system supporting the optical inspection of the inverted open microwell content.

As shown, for example in FIGS. 1, 2, and 3, in an inverted open microwell system 100, 101, the microwell 102 communicates with a microchannel 104 for carrying a fluid 130 that may contain one or more particles 128. The microchannel 104 can be associated with one or a plurality of microwells 102, for example, with one or more rows of microwells 102 in the device 100, 101.

The microchannel can be formed of a polymer, for example, polyimide, closed with a top cover 124, preferably formed of a clear material such as glass or suitable plastic, such as PMMA, polycarbonate, PEN, PET, cyclo-olefin polymer. The formed microchannel can then be adhered to the top of the microwell(s), for example, with a biocompatible adhesive.

The upper end 106 of the microwell is open to the microchannel 104. For example, fluid 130 may be caused to flow through the microchannel 104 by creating a pressure differential at each end of the microchannel 104. The microchannel 104 may be connected to a pump 132 such as a peristaltic pump, for example, or a source of pressurized air, and the like. The flow rate of fluid 130 in the microchannel can be controlled by adjusting the pressure differential between the ends of the microchannel 104, thereby controlling the rate at which particle(s) 128 pass by the microwell(s) 102.

4. Plurality or Array of Microwells

As shown in FIG. 3, the device 101 may include a plurality of microwells 102 arranged in an ordered pattern. For example, the device 101 may include an array or matrix of microwells, for example in rows and columns that may be in communication with one or a plurality of microchannels 104. The device 101 can be used to execute multiple parallel operations on a plurality of microwells 102 simultaneously. While the discussion below relates to a single microwell 102, the embodiments described are applicable to each of a plurality of microwells 102 for example, that may be disposed as an array or matrix of microwells 102 in a device 101, and may contain various configurations of microwells 102 and microchannels 104. The configuration of microwells can be designed for convenience, for example to accommodate a traditional system for transfer, such as a 96-well microtiter plate or 1536 well micro-vial assembly, and the like. The design may also be for specific purpose, such as high throughput.

5. Producing an Inverted Microwell Device

To form an inverted microwell device, in one example, microwells 102 can be produced as through holes formed through a substrate 114 with embedded electrodes 116, 118, 120. The through holes can be formed by conventional boring methods using, for example, mechanical or laser techniques. Exemplary production of an inverted microwell system is described in the Examples below.

In some embodiments, the microwells 102 have a circular or rounded cross-section, however the microwells 102 can have other cross-sectional shapes, for example, hexagonal, rectangular, square, conical, and the like shapes. The diameter of the microwell 102 is generally less than 1000 micrometers and may vary, for example, according to the dimensions of cells or other particles to be deposited in the microwell, as well as according to geometrical relationships needed to retain sufficient surface tension to form and maintain the meniscus 122. The diameter of the microwell can be, for example from about 70 μm to about 150 μm, or, for example, from about 50 μm to about 100 μm. The depth (height) of the microwell is preferably the same or greater than the diameter, and can be, for example, from about 50 μm to about 300 μm, for example from about 70 μm to 200 μm. The ratio of diameter to depth (height) can be, for example, about 1 to 1; 1 to 1.25; 1 to 1.5; or 1 to 2.

In one embodiment a device was constructed where the microchannel had a length of 27 mm, a width of 350 μm and a height of 150 μm. The microwell had a diameter of 100 μm and a height of about 75 μm. No hydrophobic or hydrophilic coatings were applied. The polyimide surfaces in the microchannel and on the bottom side of the device had a modest hydrophilic behavior as did the top side of the channel constructed with transparent polycarbonate, while the inner part of the mechanically drilled microwell, had an increased roughness that consequently increased the hydrophilic behavior of the inner part of the microwell. This difference in surface properties, where the inner part of the microwell was more hydrophilic than the microchannel and the bottom surface, combined with the proper sizing of the microchannel and the microwell, was surprisingly sufficient to allow the microwell to be properly filled with fluid from the microchannel, without producing any leakage from the bottom of the open microwell.

6. Hydrophilic/Hydrophobic Surfaces

To facilitate introduction and retention of one or more particle(s) 128 in each microwell 102, the device 100, 101 may be configured such that certain surfaces are hydrophobic while other surfaces are hydrophilic. In some embodiments, the surfaces are made hydrophobic or hydrophilic by applying a coating to the surfaces. For example, in embodiments that utilize an aqueous fluid, the bottom surface of the microchannel 143 and vertical wall of the microwell 112 may be hydrophilic and the lower surface 142 may be hydrophobic. As another example, in embodiments that utilize a lipidic fluid, the bottom surface of the microchannel 143 and vertical wall of the microwell 112 may be hydrophobic and the lower surface 142 may be hydrophilic. Kapton and Polyimide present a discrete hydrophilic behavior, with a contact angle in the range between 20 and 70 degrees. By applying a plasma surface treatment, for example an oxygen plasma, Kapton and Polyimide surfaces become more hydrophilic. Hydrophobic coatings which can be applied to Polyimide or Kapton surfaces include FEP, Certonal® FC-732 or Chemlease® 41-90.

Fluid 130, for example, a physiological buffer or culture medium, is fed into a microchannel 104 positioned above and in fluid communication with the upper open end 106 of one or more microwell 102. The micro-size of the well and hydrophobic behavior of the lower open end 108 of the microwell 102 in contrast with a hydrophilic nature of the microchannel 104 and upper end of the microwell 102, permit fluid to fill the microwell having an open bottom, without leakage from the lower open end 108. When using microwell with a closed bottom, to facilitate filling of the microwell, a wetting agent, for example ethanol or ethanol mixed with water, can be initially inserted in the microchannel prior to inserting a physiological medium is. Capillary action and surface tension retain the fluid 130 in the microwell, and form a meniscus 122 at the fluid-air interface, as shown in FIG. 1. In an embodiment, the fluid may contain a wetting agent to assist filling of the microchannel and/or microwell. Exemplary wetting agents include, for example ethanol, Tween-20, and SDS. Prior to insertion of the cell suspension, microchannels are properly rinsed with physiological medium, for example, phosphate buffer saline (PBS), to remove residuals of the wetting agents.

7. Controlled Delivery and Focusing of Particles 7.1 Controlled Delivery

A fluid containing particles, for example, cells, can be delivered to the microchannel 104 at a concentration and flow rate designed to permit a limited number of particles, for example a single particle, to be distributed into each microwell 102. Electrodes can be used to transport particles in the microchannel 104 to permit or deny access of particles 128 from the microchannel 104 into the microwell 102, to manipulate a particle(s) 128 within the microwell, to focus and hold a particle in a desired position within the microwell, to induce structural or functional changes in a particle or particles disposed within the microwell, and/or to sense and/or measure the presence, movement, or change in a particle within the microwell, or to sense and/or measure the presence of molecules produced by a particle within the microwell.

Figure 9:
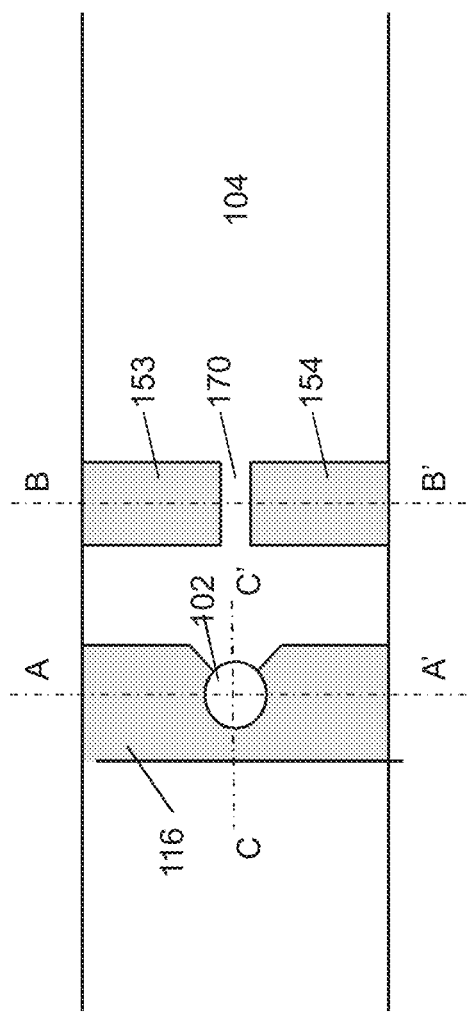
FIG. 9 is schematic drawing showing a top view of a representative arrangement of electrodes in the microchannel and microwell for controlled dielectrophoretic movement of a particle in the microchannel and at the microwell of an inverted open microwell system.

An embodiment, for example, described by FIGS. 9-11, exploits the fluid flow in the channel to transport the particles of interest from an inlet to a particular microwell, with the additional possibility to configure dielectrophoretic forces so that the particle can skip a microwell and reach another along the microchannel. An embodiment, described by FIGS. 12 and 13, shows an array of electrodes that does not require fluid flow to transport a particle in the microchannel toward a microwell, but applies dielectrophoretic forces to do so.

7.2 Transport of Particles to Microchannels in the Absence of Fluid Flow

Precise transport in microchannels for precise delivery to specific microwells is needed when a precise location for each particle is desired. One way to control precise delivery is based on a sequence of changes of electrical parameters that provides very precise results without relying on fluid flow or similar techniques.

A particle having a complex dielectric constant, when exposed to spatially varying electric fields, is pushed by negative dielectrophoresis according to the value of the Clausius-Mossotti factor. In this case, the particle will move toward the minimum of the electric field and will be repelled by the maximum of the electric field.

As shown in FIGS. 10, 11, 12 and 13, for example, electrodes 155 and 156 are positioned above the electrodes 153, 154, 157, 158, 159, 160, 161, and 162. In particular, electrode 155 is positioned above electrodes 153, 157, 159, and 161, while electrode 156 is positioned above electrodes 154, 158, 160, and 162. These electrodes can be used to create a pattern of electric field strength to cause the particle (●) 128 to move in a desired direction in the microchannel 104.

In one example, each of the electrodes 153, 157, 161, and 156 is connected to a sinusoidal voltage source at a specified electrical potential. Facing electrode partners 154, 158, 162, and 155 is each connected to a sinusoidal voltage source of the same amplitude as its facing partner, but with a phase difference of 180 degrees shift. Electrodes 159 and 160 are connected to ground (G1).

In this scenario, the electric field in the microchannel 104 reaches a minimum (Δ) 170 in the spacing between electrodes 159 and 160 as they are at the same electric potential and their thickness creates a recess that induces a strong minimum of the electric field. The electric field in the microchannel 104 reaches a maximum where electrode pairs 153-154, 157-158, 161-162 facing each other are polarized with voltages with a phase difference of 180 degrees. In this case, a particle (●) 128 is trapped in the position where the minimum (Δ) 170 between electrodes 159, 160 is surrounded by locations where the electric field reaches a maximum of intensity.

The location of the trapped particle can be changed and moved, for example, as shown in FIG. 13, toward left in two phases. During a first phase, the voltage of electrodes 157, 158 located to the left of the existing resting position is set to ground (G2). This creates a minimum (Δ) electric field that is of the same strength as that located between electrodes 159 and 160. During a second phase, electrode 159 is polarized as electrode 161 and electrode 160 as electrode 162. This polarization creates a strong electric field between electrodes 159 and 160. This field pushes out a particle trapped there that will fall in the closest minimum (Δ) of electric field, moving the particle one location to its left.

Hence, the displacement of the particles obtained in this way does not require a fluid flow.

Figure 14:
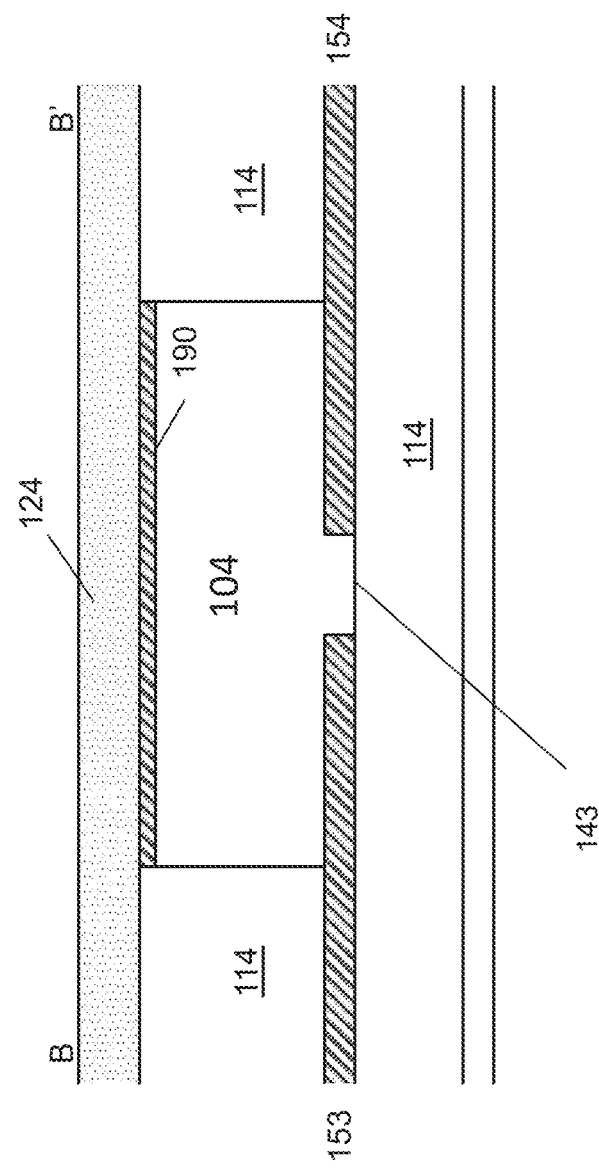
FIG. 14 is a sectional view of one embodiment, showing an alternative arrangement of electrodes in the microchannel, containing an electrode disposed along the top of the microchannel.

In another example, electrodes 155 and 156 are substituted by a unique electrode 190 positioned along the top side of the microchannel as shown in FIG. 14. The electrode 190 can be implemented either by closing the microchannel on top with a metallic material or with a transparent material, such as glass or a transparent plastic, coated with Indium Thin Oxide (ITO). This conductive coating provides an electrical connection while keeping a transparent top cover that does not prevent optical inspection or lighting from top side.

In this example, the electrode 190 is connected to ground, while each of the electrodes 153, 157, and 161 is connected to a sinusoidal voltage source at a specified electrical potential. Facing electrode partners 154, 158, and 162 is each connected to a sinusoidal voltage source of the same amplitude as its facing partner, but with a phase difference of 180 degrees. Electrodes 159 and 160 are connected to a sinusoidal voltage source of the same amplitude as the electrodes 153, 157, and 161, but with a phase difference of 90 or 270 degrees.

In this scenario, the electric field in the microchannel 104 reaches a minimum (Δ) 170 in the spacing between electrodes 159 and 160 as they are at the same electric potential and their thickness creates a recess that induces a strong minimum of the electric field. The electric field in the microchannel 104 reaches a maximum where electrode pairs 153-154, 157-158, 161-162 facing each other are polarized with voltages with a phase difference of 180 degrees. In this case, a particle (●) 128 is trapped in the position where the minimum (Δ) 170 between electrodes 159, 160 is surrounded by locations where the electric field reaches a maximum of intensity.

With this electrode configuration, the location of the trapped particle can be changed and moved, for example, toward left in two phases. During a first phase, the voltage of electrodes 157, 158 located to the left of the existing resting position is set to a sinusoidal voltage source of the same amplitude as the electrodes 153, 157, and 161, but with a phase difference of 90 or 270 degrees. This creates a minimum (Δ) electric field that is of the same strength as that located between electrodes 159 and 160. During a second phase, electrode 159 is polarized as electrode 161 and electrode 160 as electrode 162. This polarization creates a strong electric field between electrodes 159 and 160. This field pushes out a particle trapped there that will fall in the closest minimum (Δ) of electric field, moving the particle one location to its left.

FIG. 12 shows a structure that can be used to precisely deliver particles in a microwell 102 in absence of fluid flow. Electrode pair 155, 156 is not shown in FIG. 12, but as shown in FIGS. 9 and 10, the pair is located above the other electrodes, with electrode 155 in a position above electrodes 163, 116, 153, while electrode 156 is in a position above electrodes 164, 116A, 154.

If electrodes 116 and 116A are polarized at the voltage of 156 and 155 respectively, while electrodes 153 and 154 are at the same ground voltage, a particle can be trapped by negative dielectrophoresis in the location (Δ) between 153 and 154. Connecting then to ground electrodes 116 and 116A while 153 and 154 are polarized as 156 and 155, a particle is pushed toward the minimum (Δ) 170 of electric field between 116 and 116A where the microwell is located.

Since electrode 116, 116A surrounds the microwell 102 and is connected to ground, an electric field is induced in the channel beneath the microwell 102 due to the presence of electrodes 155 and 156. Following the previous analysis, the particle is now pushed toward the microwell.

In case the location where the particle descent in the microwell must be controlled in a precise way, electrode 118 can be polarized connecting it to a voltage source having amplitude substantially smaller than that used to control electrodes 155 and 156 and with a phase rotated 90 or 270 degrees with respect to electrodes 155 and 156. This polarization creates a dielectrophoretic force in the microwell that pushes the particle toward the center of the microwell.

If the delivery of the particle in the microwell must be avoided, a different polarization of the electrodes is recommended in absence of fluid flow. In particular, assuming that a particle is trapped between electrodes 153, 154 that are connected to ground, the delivery can be avoided by connecting to ground electrodes 116, 163, 164 while electrode 116A is polarized as electrode 155 and electrode 153 is polarized as electrode 156 and electrode 154 is polarized as 155. These polarizations create a temporary displacement of the particle from the location between 153 and 154 to a location toward electrode 116 (and not the location between 116 and 116A) and finally to a stable delivery position between electrodes 163 and 164 where a minimum of the electric field is located.

Figure 16:
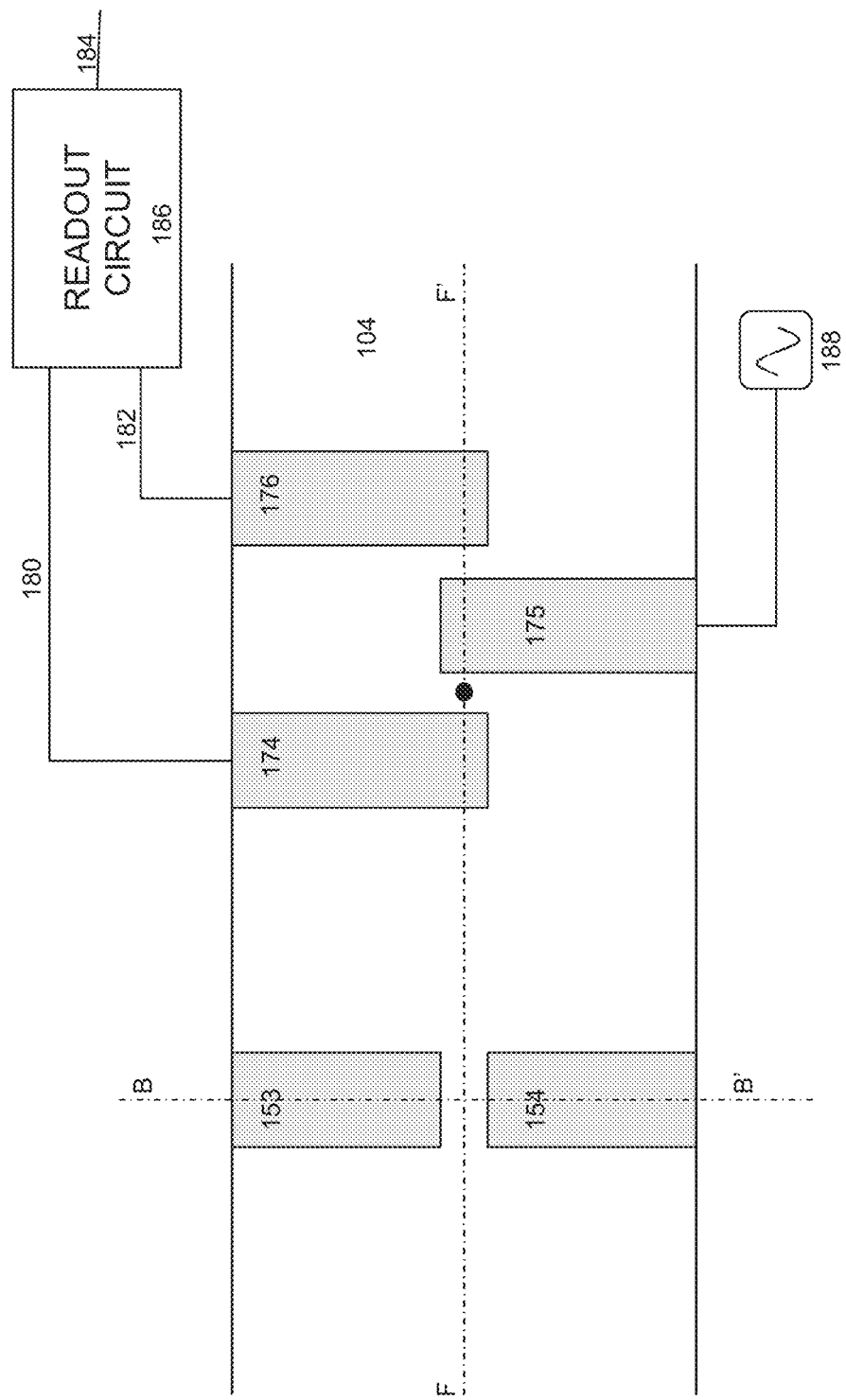
FIG. 16 shows an electrode array, according to some embodiments, centered upstream of a microwell, shown through the top of an inverted open microwell system, and demonstrating arrangement of electrodes in the microchannel for manipulating a particle (●) along F-F'.

In another example, the structure reported in FIG. 12 can be used to precisely deliver particles in a microwell 102 in absence of fluid flow. Electrode pair 155, 156 is substituted by an electrode 190 positioned on top side of the microchannel, as shown in FIG. 16, and connected to ground.

If electrodes 116 and 116A are connected to a sinusoidal voltage source of the same amplitude and a phase of 0 degrees and 180 degrees, respectively, while electrodes 153 and 154 are connected to the same sinusoidal voltage with a phase shift of 90 or 270 degrees, a particle can be trapped by negative dielectrophoresis in the location (Δ) between 153 and 154. Connecting then the electrodes 116 and 116A to a sinusoidal voltage with a phase shift of 90 or 270 degrees while 153 and 154 are connected to a sinusoidal voltage of the same amplitude and a phase of 0 degrees and 180 degrees, respectively, a particle is pushed toward the minimum (Δ) 170 of electric field between 116 and 116A where the microwell is located.

Since electrodes 116, 116A surround the microwell 102 and are connected to the same voltage, an electric field is induced in the channel beneath the microwell 102 due to the presence of electrode 190. Following the previous analysis, the particle is now pushed toward the microwell.

In case the location where the particle descent in the microwell must be controlled in a precise way, electrode 118 can be polarized connecting it to a voltage source having amplitude substantially smaller than that used to control electrodes 116 and 116A and with a phase rotated 90 or 270 degrees with respect to electrodes 116 and 116A. This polarization creates a dielectrophoretic force in the microwell that pushes the particle toward the center of the microwell.

If the delivery of the particle in the microwell must be avoided, a different polarization of the electrodes is recommended in absence of fluid flow. In particular, assuming that a particle is trapped between electrodes 153, 154 that are connected to the same sinusoidal voltage with a phase shift of 90 or 270 degrees, the delivery can be avoided by connecting electrodes 116, 163, 164 to ground while electrodes 153, 116A and 154 are connected to the same sinusoidal voltage with a phase 0, 90 and 180 degrees, respectively. Electrode 190 always remains connected to ground. These polarizations create a temporary displacement of the particle from the location between 153 and 154 to a location toward electrode 116 (and not the location between 116 and 116A). Finally, by connecting electrode 116 to the same sinusoidal voltage of electrode 153 with a phase shift of 270 degrees, the particle reaches a stable delivery position between electrodes 163 and 164 where a minimum of the electric field is located.

These structures with the voltages proposed do not rely on the presence of a flow of fluid for the displacement and delivery of particles. The fluid flow is however appropriate to provide a suitable cooling of the structure. These structures can be used to move single cells along a microchannel and drive them into an open microwell or prevent them from entering into an open microwell by properly applying a sequence of polarization signals.

7.3 Transport of Particles in Microchannels and Open Microwells in the Presence of Fluid Flow FIGS. 9-11 diagram the structure of a microwell 102 in fluid communication with a microchannel 104 closed on top by a surface 124 covering liquid contained in the microchannel. Particles such as cells or beads flowing in the channel fluid such are subjected to electromagnetic forces causing a particle 128 to be pulled toward a microwell 102 or pushed away. This structure is specifically suited to operate when there is an appreciable fluid flow in the channel that can transport the particles. See, for example, Faenza et al., 2011 (May), "Controlled isolation and patterning of k562 leukemia cells using electrically activated microchannels", In: International Conference on Microtechnologies in Medicine and Biology.

Electrodes are built into the structure of the microwell and microchannel to control particle movement. For example, FIG. 9 shows a microwell 102 surrounded by an electrode 116 shaped so that it presents an opening toward the direction of the flow in a direction that is from right to left in FIG. 9.

The specific embodiments useful to control particle movement that are shown in these Figures include those electrodes 116, 118 positioned in the microwell 102, and those electrodes 153, 154 positioned in the microchannel 104.

FIG. 10 shows a microwell 102 in communication with a microchannel 104, each having a vertical wall 112 formed by a laminate structure containing a dielectric substrate 114 and electrodes. Microchannel electrodes 153-164 are disposed in the microchannel 104 while electrode pairs 153-154 and 155-156 positioned near the junction of the microchannel with the microwell 102 at its upper open end 108. Microwell electrodes 116 and 118 are disposed near the upper end and lower ends of the microwell, respectively.

A particle (●) 128 moving in the microchannel 104 with the fluid flow is subject to a dielectrophoretic force if its complex dielectric constant is different from that of the surrounding fluid 130. Particles of interest, such as cells, microbeads or liposomes, are characterized by being driven by negative dielectrophoresis that attracts these particles towards the minima (Δ) 170 of the electric field. The particles also have a relative density higher than that of the surrounding buffer. For this reason, they fall under the effect of gravity.

FIGS. 10 and 11 show that a particle placed in the flow of the microchannel 104 encounters electrodes 153, 154, 155, 156 before reaching the microwell and electrode 116. Various configurations of applied voltages can cause a particle 128 to be trapped or ejected by an electric field, by principles of dielectrophoresis, where a particle moves in a direction toward a minima (Δ) 170 of an electrical field and away from an area with a strong electrical field.

In an example, electrode 116 is set to ground. Electrodes 155 and 156 are polarized by an external power source to a voltage generator. The voltage of electrode 155 has a phase that is rotated of 180 degrees versus that of electrode 156. Voltages applied to the electrodes 155 and 156 have the same amplitude. The voltages could change as sinusoidal signals or a square waves. For this reason, there is a relatively large electric field between the two electrodes 155 and 156.

The polarization of electrodes 153 and 154 will vary with the task of trapping or ejecting a particle. More specifically, electrodes 153 and 154 can be connected to ground in a configuration that is called "trapping". Alternatively, electrodes 153 and 154 can be polarized with sinusoidal voltages or square waves. When they are polarized, the phase of electrode 153 will be the same of that of electrode 156, while electrode 154 will have the phase of electrode 155. This second configuration is called "ejecting". Refer to FIG. 11 for the relative location of the electrodes.

Following the electrode configuration shown in FIGS. 9-11, when a desired particle 128 flowing in the microchannel 104 is to be trapped in a microwell 102, electrodes 153 and 154 are set at the ground potential. Electrodes 155 and 156 are polarized by an external power source to a voltage generator. The voltage of electrode 155 has a phase that is rotated of 180 degrees versus that of electrode 156. Voltages applied to the electrodes 155 and 156 have the same amplitude. The voltages could change as sinusoidal signals or a square waves. For this reason, there is a relatively large electric field between the two electrodes 155 and 156.

In this condition, a "trapping" situation exists, since the electric field reaches a strong minimum in the location 170 placed between electrodes 153 and 154. The remaining region in the channel is subject to a stronger electric field that pushes the particle towards the minima (Δ). The thickness of electrodes 153 and 154 as well as all other electrodes is about 5 to 30 microns. This creates a region (Δ) 170 where the field reaches a minimum, and where the particles have approximately the same size of the surrounding electrodes.

Region (Δ) 170 is aligned to the opening of the microwell 102. A particle trapped at the minima region (Δ) 170 is pushed by the fluid flowing in the microchannel toward the opening of the microwell along a horizontal path. The distance between this region (Δ) 170 and the opening of the microwell 102 is kept to a value as small as feasible given the manufacturing technology. If a standard Printed Circuit Board technology is used, a distance of about 20 to 100 microns is typical. Since electrode 116 surrounds the microwell 102 and is connected to ground, an electric field is induced in the channel beneath the microwell 102 due to the presence of electrodes 155 and 156. Following the previous analysis, the particle is now pushed toward the microwell.

In case the location where the particle descent in the microwell must be controlled in a precise way, electrode 118 can be polarized connecting it to a voltage source having amplitude substantially smaller than that used to control electrodes 155 and 156 and with a phase rotated 90 or 270 degrees with respect to electrodes 155 and 156. This polarization creates a dielectrophoretic force in the microwell that pushes the particle toward the center of the microwell.

If a particle flows in the microchannel 104 and it is not intended for microwell 102, the desired effect can be achieved by polarizing the electrodes 153 and 154 in the "ejecting" configuration. In this case, the minimum of the electric field is placed in the middle of the microchannel 104. In this location, the particle is exposed to the fluid flow and is not trapped by the microwell 102 if the distance between the microwell 102 and electrodes 153 and 154 is small.

In another example the controlled movement of the particle can be obtained by initially trapping a particle between electrodes 153 and 154 and then programming the "loading" or "ejecting" configuration by properly setting the polarization of electrodes 153, 154 and 116 while keeping electrode 155 constantly connected at a sinusoidal voltage and electrode 156 connected at the same sinusoidal voltage of electrode 155 shifted by 180 degrees. In order to initially trap the particle, electrodes 153 and 154 are tied to ground, and electrode 116 is connected to the same sinusoidal voltage of electrode 155 shifted by 90 degrees. By setting a fluid flow directed from electrodes 153 and 154 towards the microwell, it is possible to find a value of the flow which is low enough for trapping a particle in the minimum of the electric field located between electrodes 153 and 154 with a drag force which is not sufficient for moving forward the particle and contrast the electric field created between electrode 116 on one side and electrodes 155 and 156 on the other side. If the particle needs to be delivered to the microwell, then the electrode 116 is connected to ground and the drag force will move the particle towards the microwell and then into the microwell. If, instead, the particle has to move forward, bypassing the microwell, electrodes 153 and 116 are connected at the same sinusoidal signal of electrode 156, while electrode 154 is connected at the same sinusoidal voltage of electrode 155. In this configuration, the particle first moves upwards and then towards the portion of electrode 116 under electrode 156, where a minimum of the electric field is located. In this way the microwell is circumvented and the particle is not delivered. Assuming now to have a second microwell following along the channel, with the same architecture illustrated in FIG. 9, a new set of electrodes 153 and 154 can be set to ground and the electrode 116 of the first microwell can return to the initial voltage. In this way the minimum is now located between the couple 153, 154 of the second microwell and the particle will position between these electrodes. This scheme can be repeated for several wells positioned along the same microchannel.

7.4 Detection of Particles in a Microchannel

Figure 15:
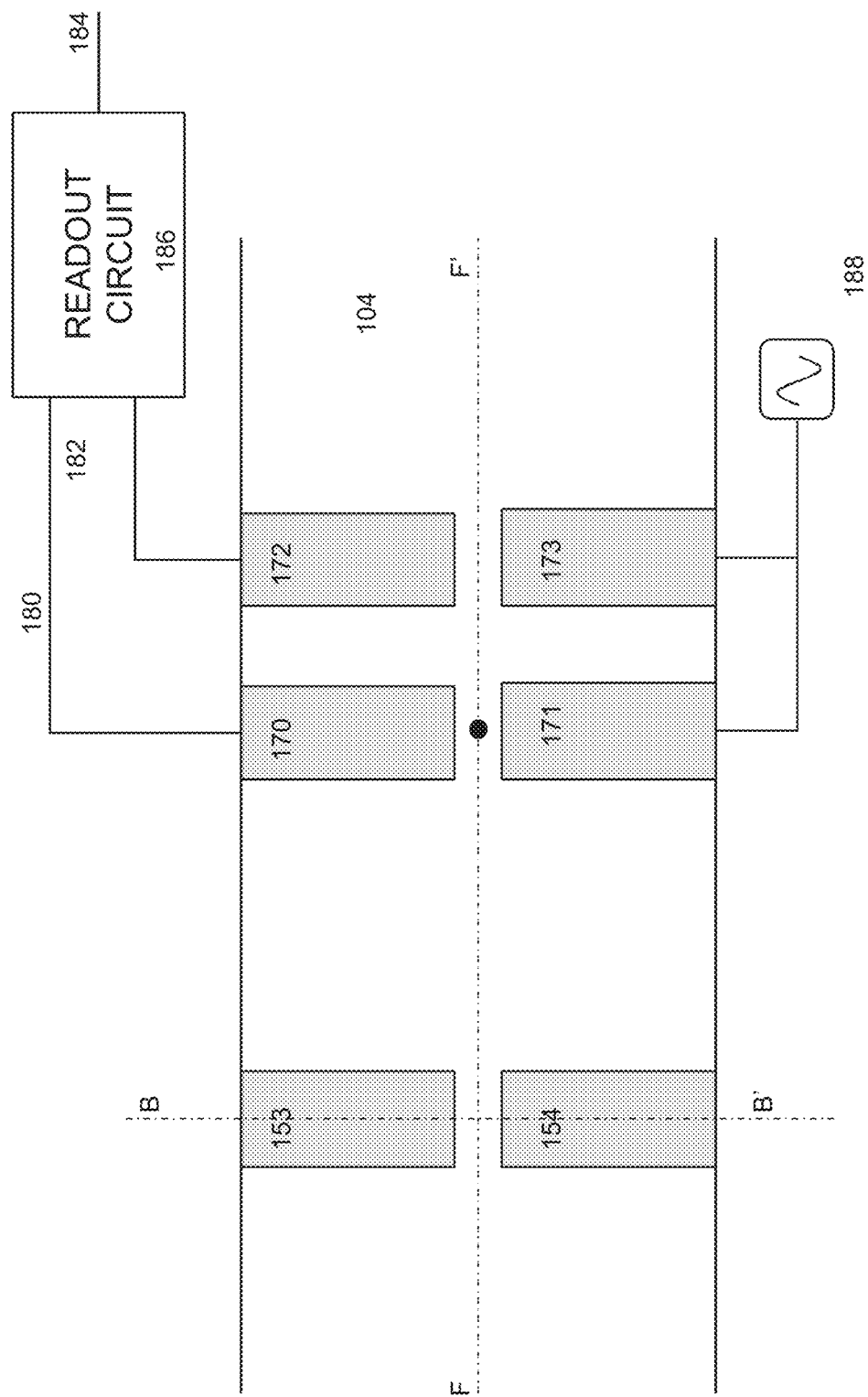
FIG. 15 shows an electrode array, according to some embodiments, centered upstream of a microwell, shown through the top of an inverted open microwell system, and demonstrating arrangement of electrodes in the microchannel for manipulating a particle (●) along F-F'.

When a particle (●) in a microchannel 104 is manipulated by the electrodes shown in FIGS. 9-14 in such configurations allowing the particle to be delivered into a target microwell, the electrodes produce the effect of aligning the particle along the axis F-F' as shown in FIGS. 15-16. Moreover the particle is vertically pushed onto the bottom side of the microchannel. The precise positioning of particles along a predefined axis and at a precise vertical location make them suitable to be detected either optically or by impedance measurement, assuming a continuous laminar fluid flow is present in the microchannels and with the effect of dragging the particle along the F-F' direction. The benefit of implementing cell focusing through dielectrophoresis to improve optical detection and cell delivery in microwell is demonstrated, for example, in Duqi et al., 2011 (May), "Automated isolation of a programmable number of cells into microwells using DEP forces and optical detection", International Conference on Microtechnologies in Medicine and Biology.

In one embodiment, a structure composed of four electrodes 170, 171, 172, 173 is properly positioned downstream to the manipulation electrodes 153, 154 as shown in FIG. 15. Electrodes are designed as to allow the particle moving along the F-F' direction to pass through the gap between electrodes 170-171 and 172-173. Electrodes 171, 173 are connected to an excitation signal 188 represented by an alternate voltage, while electrodes 170, 172 are connected to a readout circuit 186 which amplifies the output currents 180 and 182 and provides a final output signal 184 proportional to the difference or the ratio between signals 180, 182. This is accomplished by using known circuit schemes. The presence of upstream electrodes 153, 154, 155, 156 has the effect of aligning cells along the axis where the signal-to-noise ratio produced on the output signal 184 by the passage of single cells is maximum.

In another embodiment, the detection of a single cell after proper positioning and alignment performed by electrodes 153, 154, 155, 156, is performed by means of a structure composed of three electrodes 174, 175, 176, as shown in FIG. 16. Electrode 175 is connected to an excitation signal 188 represented by an alternate voltage, while electrodes 174, 176 are connected to a readout circuit 186 which amplifies the output currents 180 and 182 and provides a final output signal 184 proportional to the difference or the ratio between signals 180, 182. The presence of upstream electrodes 153, 154, 155, 156 has the effect of aligning cells along the axis where the signal-to-noise ratio produced on the output signal 184 by the passage of single cells is maximum.

In one embodiment the detection of single cells after proper positioning and alignment performed by electrodes 153, 154, 155, 156 is performed by optical detection, either under fluorescence or normal lighting conditions, by positioning an optical excitation and detection system on top or bottom side of the microwell array and by aligning the optical system along the axis F-F'.

Once the particle is detected according to one of the methods previously described, in a specific embodiment the structure represented by electrodes 116, 153, 154, 155, 156, 116, 118 and the microwell 102 and reported in FIGS. 9-11 is duplicated and positioned downstream of the detection region or electrodes. The control of these electrodes is dependent on the sensing signal 184 obtained by optical or electrical measurement, in such a way that a single cell, when detected, can be selectively pulled into a target microwell or pushed away from it. This embodiment enables the precise positioning of single cells or a predetermined number of cells in microwells.

7.5 Focusing of Particles in a Microwell

When a particle 128 enters a microwell 102, gravity causes the particle 128 to descend through the microwell 102 toward the meniscus 122. To assure that the particle 128 remains substantially centered in the microwell 102, microwell electrodes 116, 118, 120 may be powered to force the particle 128 to a central position across the diameter of the microwell 102. For example, the voltages applied to the electrodes 116, 118, 120 may be controlled to generate a substantially zero or substantially vertical electric field at or near the vertical axis of symmetry of the microwell 102. This results in the particle 128 being forced to the center of the microwell 102, causing the particle 128 to descend the length of the microwell along a central axis, depositing at or near the center of the meniscus 122. Descent of the particle may be facilitated by gravity or by electromagnetic forces, or a combination of these.

While the microwell electrodes 116, 118, 120 are shown as annular electrodes, in some embodiments the microwell can include pairs of electrodes, for example, facing electrodes, to effect particle manipulation and movement within the microwell. In addition, the microwell may contain additional electrodes, including for example, electrodes useful in a particular analysis or reaction, such as sensing and/or measuring electrodes for sensing particles, products of cells, and cellular changes. Sensing or measurement electrodes can be used, for example, to measure changes in impedance, optical signal, polarity, and the like electrical signals A particle 128 deposited on the meniscus 122 remains stably positioned on the meniscus 122 even after electromagnetic forces, for example, voltages applied to the electrodes are suspended. Exemplary approaches to applying voltages to the electrodes to manipulate particles with dielectrophoresis are described in published U.S. Patent Application No. 2009/0288963, incorporated herein by reference in its entirety.

When a particle 128 has entered a microwell 102, electrodes 153 and 154 positioned on the bottom side of the microchannel near the junction between the microwell 102 and the microchannel 104 may be powered to prevent additional particles flowing in the microchannel from entering the microwell. For example, the phase of the voltage applied to the electrodes 153 and 154 can be controlled to repel other particles in the fluid, essentially closing the microwell 102. This may occur after the particle has dropped past the electrode 116, for example, while electrodes 118 and 120 may be employed to center the particle in the microwell, permitting the particle to descend the length of the microwell by gravity, and remaining substantially in a central position, even in the absence of applied electromagnetic force.

In some embodiments, two or more particles 128 are permitted to enter the microwell 102 and are positioned so as to force the particles into contact or into close proximity with each other. For example, after a first particle 128 has been positioned on the meniscus 122, the voltage applied to the electrodes 153 and 154 may be removed, opening the microwell 102 for receipt of one or more additional particle from the microchannel 104. When one or more additional particle(s) enter the microwell 102 from the microchannel 104, the additional particle(s) 128 may be centered in the microwell 102 by applying voltages to electrodes 118, 120 as discussed above. The additional particle(s) 128 descends along a vertical axis of symmetry 110 of the microwell until the additional particle(s) is positioned in contact or in close proximity to the particle 128 on the meniscus 122. In alternative embodiments, all particles are introduced into the microwell at substantially the same time, and the electrodes 116, 118, 120 are powered to focus the particles to the center of the microwell as an aggregate group of cells, forming a cluster of deposited cells at the meniscus.

8. Observing Deposited Cells Microscopically

Because of the open nature of the microwells 102, it is possible to observe the docking of a particle 128 on the meniscus 122 at the fluid/air interface at the lower end 108 of the microwell 102, for example, using a microscope, camera, or other optical device. The particle(s) 128 can be viewed from either the upper end 106 of the microwell 102, for example through the microchannel 104 and a top cover 124 that may be fabricated with a transparent material such as glass or plastic, or viewed from the lower end 108 of the microwell, for example, where the view is not impeded.

9. Stable Retention at the Meniscus

Surprisingly, particles, including living cells, are stably retained on the meniscus when the electric field is deactivated, and while fluid is continuously flowing in the microchannel and thereby into the microwells. It has been surprisingly found that cells disposed on the meniscus are not dislodged by fluid washes or changes in media in the absence of an electric field, assuming a proper sizing of the microwell. This stable retention permits removal of harmful fluids, for example buffers and reagents needed for DEP manipulations, and permits replacement with fresh buffers and culture media more suitable for maintenance and vitality of deposited biological particles and/or more suitable for particular analytical procedures within the microwell.

Stable retention on the meniscus can be achieved if the shear stress induced by the horizontal component of the fluid velocity is relatively low or null at the bottom level of the microwell. By changing the relative ratio between the diameter and depth of closed microwells the horizontal component of the fluid velocity changes as well, as explained in Han et al., 2010, "Integration of single oocyte trapping, in vitro fertilization and embryo culture in a microwell-structured microfluidic device," *Lab on a Chip*, vol. 10, no. 21, pp. 2848-2854. A similar behavior is observed in inverted open microwells where the bottom side features a meniscus between the air and the fluid.

In one embodiment, the microwell is sized as to ensure a depth equal or higher than the diameter. For instance, a depth of 100 microns or more for a diameter of 75 microns is considered. This microwell sizing allows to maintain a horizontal fluid velocity of less than 1 micron/sec for an average fluid speed of 2.5 mm/sec in the microchannel.

A continuous supply of nutrients in buffer or media flowing in the microchannel, as well as removal of catabolites produced by the cells is possible in the inverted open microwell system, and helps to maintain the viability of the cells or other particles disposed in the microwell. In addition, exposure to the atmosphere outside the device at the lower end open of the microwell permits exchange of gases, contributing to maintaining the health and viability of the particle or particles contained in the open microwell.

Surprisingly, in the inverted open microwell system, a combination of features, including small volume, stable retention, efficient buffer and media exchange, efficient gas exchange, and the ability to manipulate and focus cells to a desired position with minimum use of electromagnetic forces, permits not only efficient use of the system to evaluate characteristics of single cells, but also to retain, reuse, and recover the original cells for clonal expansion.

10. Recovery of Microwell Contents

In an embodiment, the contents of the microwell can be recovered, for example, by disrupting the surface tension at the meniscus. Disruption of surface tension can be accomplished, for example, by applying a pressure pulse to the microchannel 104, for example, from a pump 132 or a source of pressurized air, and the like, with a pressure ranging from 0.5 bars to 3 bars and a pulse duration ranging from 1 millisecond to 100 milliseconds. The contents of the microwell are released, for example, as a droplet 138 containing, for example, a single particle, cell, or cluster of particles or cells, in fluid of the microwell, into a suitable receptacle 126, for example a reservoir, microtiter plate, collection vial system, capture surface, and the like, positioned under the microwell 102 (FIGS. 4, 5). In an embodiment, the receptacle 126 can include a filter or membrane for separating particle(s) from fluid recovered from the microwell 102.

In an embodiment, fluid surrounding a particle 128 in the microwell can be concentrated by evaporation prior to recovery from the microwell. For example, replacing the fluid in the microchannel with air or suitable gas can result in reduced volume in the microwell, as evaporation will occur at the lower end 108 of the microwell open to air or gas. Applying pressure to the air/gas in the microchannel can cause release of the concentrated fluid in the microwell to be released into the receptacle(s).

In one embodiment, the microwell contains a semipermeable membrane 134 at or near the air/fluid interface at the lower end of the microwell, the membrane retaining the particle(s). In this embodiment, fluid can be recovered from each microwell 102 into the receptacle(s) 126.

Where the device 101 contains a plurality of microwells, the content of multiple wells can be transferred to a matched set of multiple receptacles in parallel, for example to multiple wells of a microtiter plate.

During transfer of a cell from the microwell, it may be possible that other cells or particles are trapped in the microchannel and may be transferred along with the cell(s) in the microwell when the pressure pulse is applied. To limit this problem, a bovine serum albumin (BSA) coating or other anti-stiction coating, for example, an organic passivation layer such as a fluorinated fatty acid self-assembled monolayer (SAM) or alkylhalosilane can be added to the microchannels prior to use.

EXAMPLES

The invention may be more fully understood by reference to the following Examples. The examples are meant to describe specific exemplary embodiments of the invention and are not meant to limit the scope of the invention.

Example 1

Analysis of Fabricated Microchannel and Microwell Geometries 1.1 Fabrication

A device containing a plurality of open microwells was created by drilling through holes through a multilayer flexible printed circuit board (PCB) substrate. The dimensions of the microwells were varied to analyze the effectiveness of specific geometries of the microwells. In this study, the diameter of the drilled holes ranged from 70 µm to 150 µm, PCB thickness was between 75 μm and 350 μm, and each device included a matrix of 6×6 or 8×8 holes. Preferred implementations were prepared as shown below in Table 1 in order to directly interface the open microwell array to standard microtiter plates and easily perform the recovery and transfer of cells into microtiter wells.

Microchannels 104 having a thickness ranging from 30 μm to 200 μm and a width ranging from 200 μm to 1 mm were fabricated of polyimide, on the top side of the plurality of microwells 102, disposed above the upper end 106 of the microwells. A channel cover 124 was formed of transparent polycarbonate, having a thickness of 750 μm by adhering it atop the microchannel.

TABLE 1

Microwell arrays features

| Number of microwells | Rows × Columns | Well-to-well and channel-to-channel pitch |
|---|---|---|
| 24 | 6 × 4 | 18 mm |
| 96 | 12 × 8 | 9 mm |
| 384 | 24 × 16 | 4.5 mm |
| 1536 | 48 × 32 | 2.25 mm |

Microchannel walls were fabricated in polyimide and bonded to a top cover using an adhesive properly cured at a temperature of 70° C. for 2 hours until overnight, in order to ensure the biocompatibility of the adhesive, or using an adhesive laminated at room temperature and then coated with BSA 1 mM to ensure biocompatibility.

In an alternative embodiment, a photosensitive polymer film (Ordyl SY550, Elga Europe) having a thickness of 55 μm was attached to a glass top cover and structured to create the microchannel, before attaching it to the underlying flexible PCB containing the drilled microwells. Holes were formed in the top cover to provide input and output fluidic connections or embedded fluid reservoirs. The holes had a diameter of about 0.45 mm.

Fluid or fluid containing cells and particles were inserted in each microchannel using a peristaltic pump (Watson Marlow 101U/R) connected as shown in FIG. 5 in one study, and using a syringe pump connected to the microchannel inlet (KDS-210, KD Scientific, Holliston, Mass.) in another. Fluid flow ranged from 1 microliter/hour to 20 microliters/minute, depending on the channel section and the specific operation to be executed on the particles. Fluid leakage from the lower end of the microwells was prevented by the capillary forces acting in the microwells. In some cases a hydrophobic coating (Certonal® FC-732) was added on the bottom surface of the device to increase the resistance to fluid leakage. As a result, the fluidic system provides fluid in the microchannel that surprisingly fills the microwells without leaking from the lower end.

1.2 Analysis of Cells Deposited by Gravity

Live K562 cells (immortalized human myelogenous leukemia cells) were suspended in physiological solution (NaCl 0.9% w/v or PBS) at a concentration of $1.6 \times 10e6$ cells/milliliter and inserted into a microchannel of an inverted microwell device using a peristaltic pump. The microchannel width was 600 μm and the height was 55 μm, and each microwell had a diameter of 70 μm.

The input pump was set to operate in cycles where each cycle was composed of two phases. During Phase 1 the fluid was active for 1 minute at a speed of 9 microliters per minute, while during Phase 2 the pump was deactivated for a period of 1 minute and 30 seconds. During Phase 1 cells flowed in the channel along random trajectories. At the beginning of Phase 2 cells were stationary in the channel in random locations. During Phase 2 a certain number of cells were allowed to enter into each microwell by sedimentation.

Using an inverted microscope, the content of each well was checked and the possible presence of a cell in the microwell as a consequence of sedimentation was detected. The results demonstrated that it is possible to control the distribution of cells entering into the microwells by adjusting the cell concentration. In the condition here described we obtained the distribution reported in Table 2.

TABLE 2

Loading efficiency of cells in microwells
(total of 41 samples)

| Number of cells loaded | Frequency |
|---|---|
| 0 | 51% |
| 1 | 42% |
| 2+ | 7% |

The result of the load phase demonstrated that a single cell or multiple cells can be deposited in a microwell reaching the air fluid interface at the lower open end and can remain there trapped and alive, and without breaking the surface tension of the meniscus. In those microwells where no force but gravity was applied to the cells during their descent into the microwell, the position of the cell(s) deposited on the fluid meniscus was random (See FIG. 6A).

1.3 Analysis of Cells Deposited by Focused Alignment and Gravity

Using two or more electrodes, as shown in FIG. 2, it is possible to generate a dielectrophoretic force acting on particles within the microwell, and to manipulate the particles along a vertical axis of the well during their descent from entry from the microchannel 104 at the upper open end 106 of the microwell down to the lower open end 108. In each pair of adjacent electrodes 116, 118, 120, a first electrode is connected to a sinusoidal signal, while a second electrode is connected to ground or to the same sinusoidal signal with a phase rotation of 180 degrees.

An inverted microwell system was constructed and used for this study, having the features of the system shown in FIG. 2. The microwell 102 had a diameter between 100 μm and 120 μm and the vertical spacing between each pair of annular electrodes 116, 118, 120 was 50 μm.

K562 cells were suspended in a 1:9 mixture of PBS and glycerol (300 mM). Electrodes 116 and 120 were connected to the same sinusoidal voltage with a typical frequency included between 80 KHz and 100 KHz. The amplitude of the applied voltage ranged between 3.4 V and 15 V. Electrode 118 was tied to ground. As a result of loading four cells into the microwell while keeping the electric field activated, each of the cells was effectively forced to align along the central axis of the microwell. On reaching the air/fluid meniscus at the lower end of the microwell, each cell was centrally placed and in contact with the prior loaded cell(s). The aggregation is due to a combination of vertical gravity force and the horizontal component of the dielectrophoretic force.

The open microwell was observed with an inverted microscope 140 under fluorescence conditions. When electrodes in the well were properly polarized, one or more cell was focused to a center axis of the microwell. The cells, so aligned during descent along the central axis, were each centrally deposited on the meniscus 122 of the microwell, forming an aggregate at the air-fluid interface and resulting in cell to cell contact.

Figure 6B:
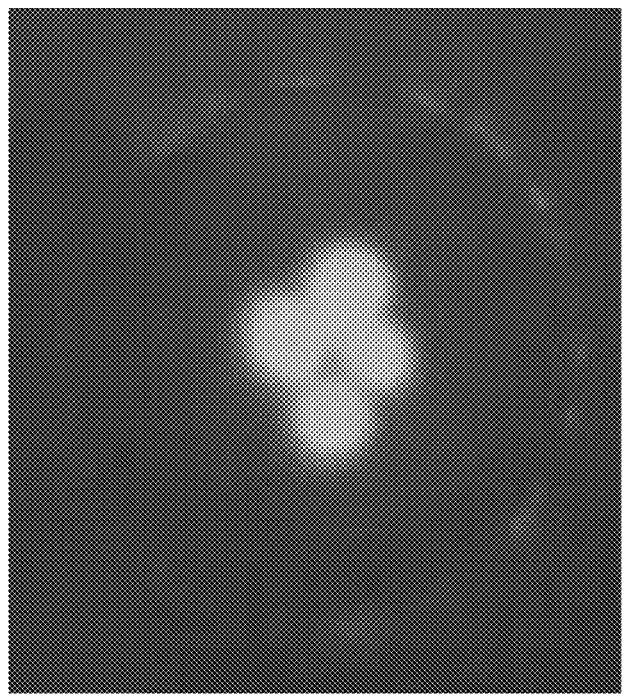
FIGS. 6A and 6B show photographs of the meniscus of an inverted open microwell observed with an inverted fluorescence microscope showing (FIG. 6A) K562 cells positioned randomly at the meniscus when no electric field was applied to focus the cells during descent and (FIG. 6B) K562 cells manipulated by electromagnetic forces to a central vertical axis of the microwell during descent and deposited as an aggregate of cells near the center of the meniscus.
Figure 6A:
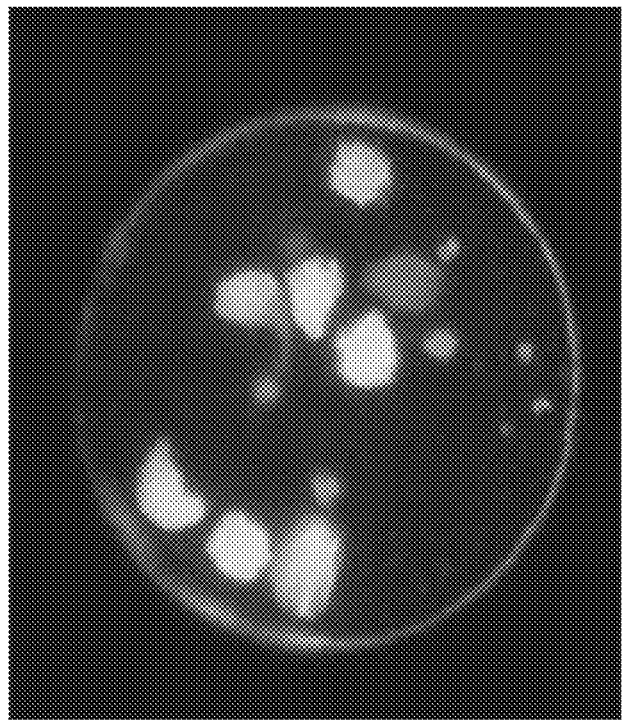

K562 cells were labeled with a fluorescent dye and viewed with an inverted microscope. As shown in FIGS. 6A and 6B, while the cells were randomly deposited on the meniscus of the microwell by gravity when no electric field was applied (FIG. 6A), the same cells deposited by combination of vertical gravity and dielectrophoretic force formed an aggregate of particles deposited at a central portion of the meniscus (FIG. 6B).

1.4 Analysis of Microbeads Deposited by Focused Alignment and Gravity

Polystyrene microbeads with a diameter of 10-25 µm were suspended in deionized water or glycerol at 22.5 mM and delivered by gravity to microwells having a diameter of about 80 µm. Electrodes 116 and 118 were connected to the same sinusoidal voltage with a frequency of 100 KHz. Electrode 117 was tied to ground. The focusing of aggregates of 2 beads was analyzed and results, showing the average bead to bead distance and the relative number of bead-bead contacts created as a function of the signal amplitude, are reported in Table 3.

TABLE 3

| Voltage Amplitude (V) | Average distance (µm) | Rate of bead-bead contacts |
|---|---|---|
| 2 | 7.2 | 33% |
| 4 | 2.2 | 90% |

1.5 On-Chip Labeling of Cells Trapped on the Meniscus

The impact of changing fluid in the microchannel on the fluid surrounding cells trapped on the meniscus at the distal end of the open microwell was analyzed to determine the ability of the inverted open microwell system to provide a single-cell centrifugation function. A calcein staining protocol was executed on K562 cells.

K562 cells were delivered to inverted open microwells by limited dilution and sedimentation. After cell delivery to the meniscus, the microchannel was rinsed by flowing PBS in the microchannel for five minutes. A buffer containing calcein (1 mM in NaCl 0.9% w.v), a tracer molecule that becomes fluorescent when taken up into cells, was continuously flowed in the microchannel for 40 minutes at a constant flow rate of 9 microliters per minute. Table 4 shows the dynamic profile of fluorescence intensity monitored in single cells within the microwells.

Cell staining was effective and demonstrated diffusion of calcein from the microchannel into the microwell and into the stably retained cells. The cells were surprisingly retained at the meniscus after washes, and were viable, as demonstrated by calcein uptake. By monitoring calcein uptake on single cells, it was possible to observe different uptake profiles. On average, maximum uptake was achieved after 30-40 minutes. Fluorescence intensity is shown in the Table 4.

TABLE 4

| Time (minutes) | Cell 1 | Cell 2 | Cell 3 | Average | CV % |
|---|---|---|---|---|---|
| 2 | 5.8 | 4.2 | 19.0 | 9.6 | 84 |
| 4 | 7.9 | 13.1 | 24.3 | 15.1 | 55 |
| 6 | 7.7 | 17.8 | 30.3 | 18.6 | 61 |
| 8 | 10.9 | 22.4 | 33.6 | 22.3 | 51 |
| 10 | 14.2 | 27.6 | 37.4 | 26.4 | 44 |

TABLE 4-continued

| Time (minutes) | Cell 1 | Cell 2 | Cell 3 | Average | CV % |
|---|---|---|---|---|---|
| 12 | 19.7 | 32.5 | 41.4 | 31.2 | 35 |
| 14 | 23.9 | 37.0 | 44.4 | 35.1 | 30 |
| 16 | 28.9 | 39.5 | 47.5 | 38.7 | 24 |
| 20 | 38.9 | 45.4 | 53.3 | 45.9 | 16 |
| 25 | 52.3 | 58.7 | 65.4 | 58.8 | 11 |
| 30 | 61.9 | 62.5 | 63.5 | 62.6 | 1 |
| 40 | 74.0 | 60.5 | 44.6 | 59.7 | 25 |

Example 2

2.1 Recovery of K562 Cells after Delivery and DEP Focusing

Use of the inverted open microwell system for analysis of single cell function permits recovery of cells determined to have desired properties. After trapping single cells and/or particles, for example, each in one of a plurality of microwells, for example in a microwell array, cellular function can be analyzed by one or more bioassays. When a particular cell is identified as having one or more desired characteristic or function, the content of each microwell can be recovered and transferred to a substrate such as a microtiter plate.

A device having the features shown in FIG. 5 was developed to enable cell recovery from the inverted open microwell. To release contents of the microwells, a pressurized filtered gas such as nitrogen or air is inserted into the microchannel 104 in a controlled manner. For example, a pulse of pressure of about 1 bar was be applied through a connection at the input of a normally closed electro-valve 172.

An electronic system connected to the control input of the electro-valve 172 generated voltage or current pulses with a duration of about 5 milliseconds. On generation of a pulse, the pressurized gas entered the microchannel 104 via tubing connecting the microchannel input and output port, and as a result, a fluid droplet 138 was ejected from each microwell 102 and spotted onto a receptacle 126, represented by a capturing surface in some experiments or a microtiter plate in other experiments, where the plate was positioned under the microwell array and properly aligned. One or more particles and/or cells present in the microwell were transferred to the capture surface in droplets 138 of fluid.

During transfer of a cell from the microwell, it may be possible that other cells or particles are trapped in the microchannel and may be transferred along with the cell(s) in the microwell when the pressure pulse is applied. To limit this problem, a bovine serum albumin (BSA) 1 mM coating was inserted into the microchannels for 30 minutes for prior to use, in order to form a protein self-assembled monolayer. The microchannel was rinsed with PBS for 20 minutes before cell recovery. All of the cells had been removed from the microchannel so that only the cells contained in the microwell were transferred to the recovery receptacle.

2.2 Viability and Growth of Recovered Cells

One function of the inverted microwell system is to assess the function of a single cell or cells, and to recover from the microwell or expand within the microwell, viable cells identified as having a desired functional property. The viability of cells under activated or inactive electric fields and DEP as well as for different lengths of time can be assessed, for example, by monitoring the growth and expansion of recovered single cells or small cell clusters, for example, counting cell number daily. Cell growth can also monitored by viewing cells with a microscope.

Single K562 cells were suspended in physiological medium and cells were delivered to microwells by sedimentation, and deposited on the air/fluid meniscus in a plurality of microwells. After 20 minutes, the individual cells were transferred as described above by delivering a pressure pulse to the fluid in the channel, thereby causing transfer of a droplet containing the cell from the microwell to a well of a 96 well microtiter plate having V-shaped wells filled with RPMI growth medium supplemented with Fetal Calf Serum. After a few hours of incubation, the single cell sedimented into the V-shaped well, and was observed with an inverted microscope.

Figure 8:
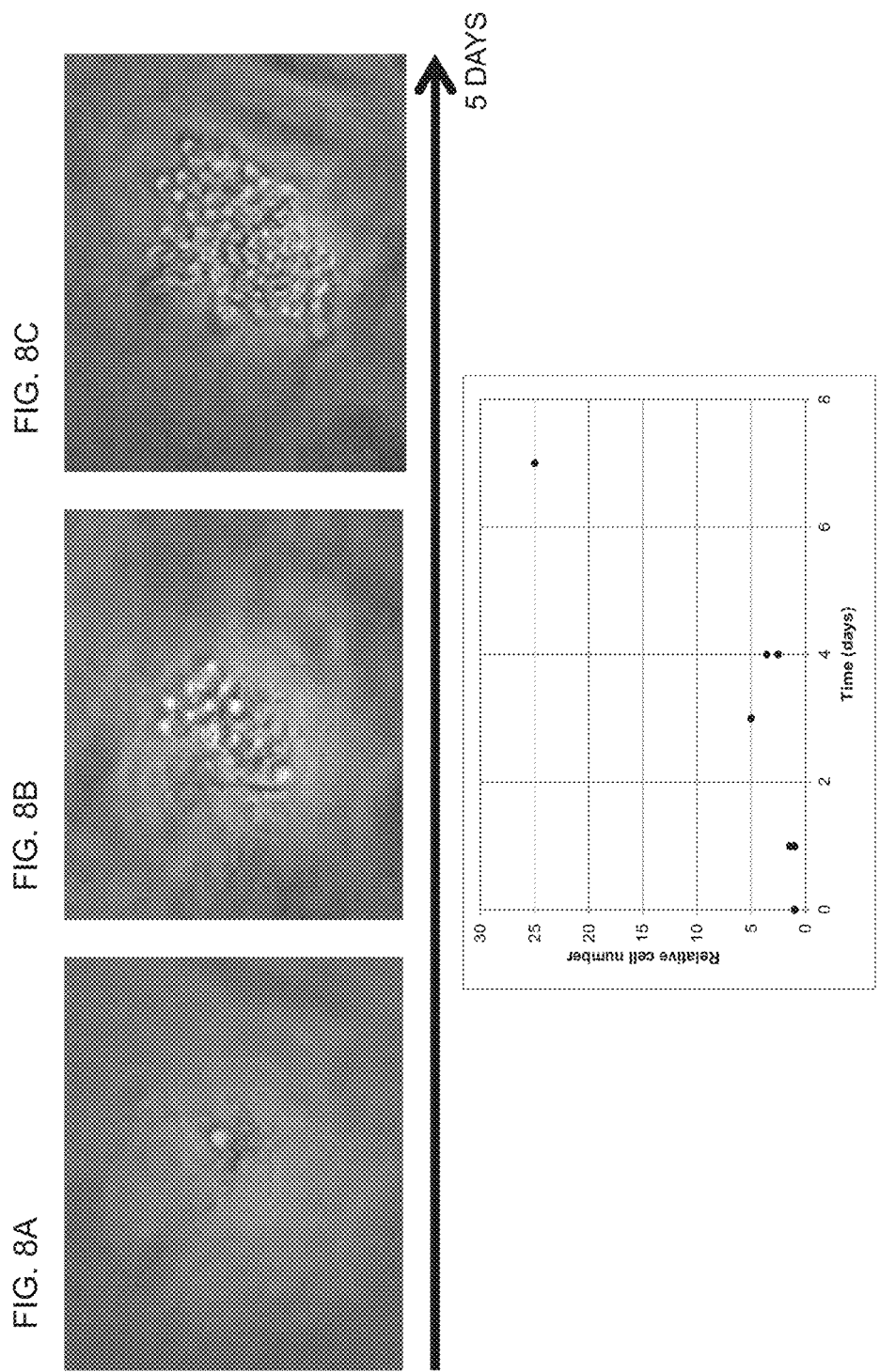
FIGS. 8A-8C show a series of photographs demonstrating clonal expansion of a single K562 cell recovered from an open microwell after dielectrophoretic positioning and transferred to V-shaped microtiter plates for expansion over 5 days.
FIG. 8D is a graph showing an increase in relative cell number over a period of six days.

The cells were incubated at 37 degrees C. with 5% $CO_2$ and cultured for several days. Viewing the cell cultures each day confirmed the growth of a clonal cell population from each of the single cells recovered. After 3-5 days cell growth and expansion was demonstrated and a monoclonal cell line had been generated from the single deposited cell. Growth of the single cell or small aggregates of cells is shown in a series of timed photographs and reported as a graph in FIG. 8D. This study demonstrates that deposition of cells on the meniscus of an inverted open microwell and recovery of the cells was possible, and permitted recovery of viable cells.

Example 3

Cell-Cell Interaction Analysis 3.1 Activity of CTL Cells Against Target LCL Cells Functional live cell-cell interactions in the inverted microwell system were demonstrated by induction of cell lysis by T-lymphocytes on target tumor cells. Target cells, LCL cells, were marked with calcein and delivered to microwells. T-lymphocytes (CTL) were activated against the target cells and delivered to the same microwells. Fluorescence of the target cells was monitored by fluorescence microscopy and the calcein fluorescence profile was determined as a measure of cell lysis.

Figure 7:
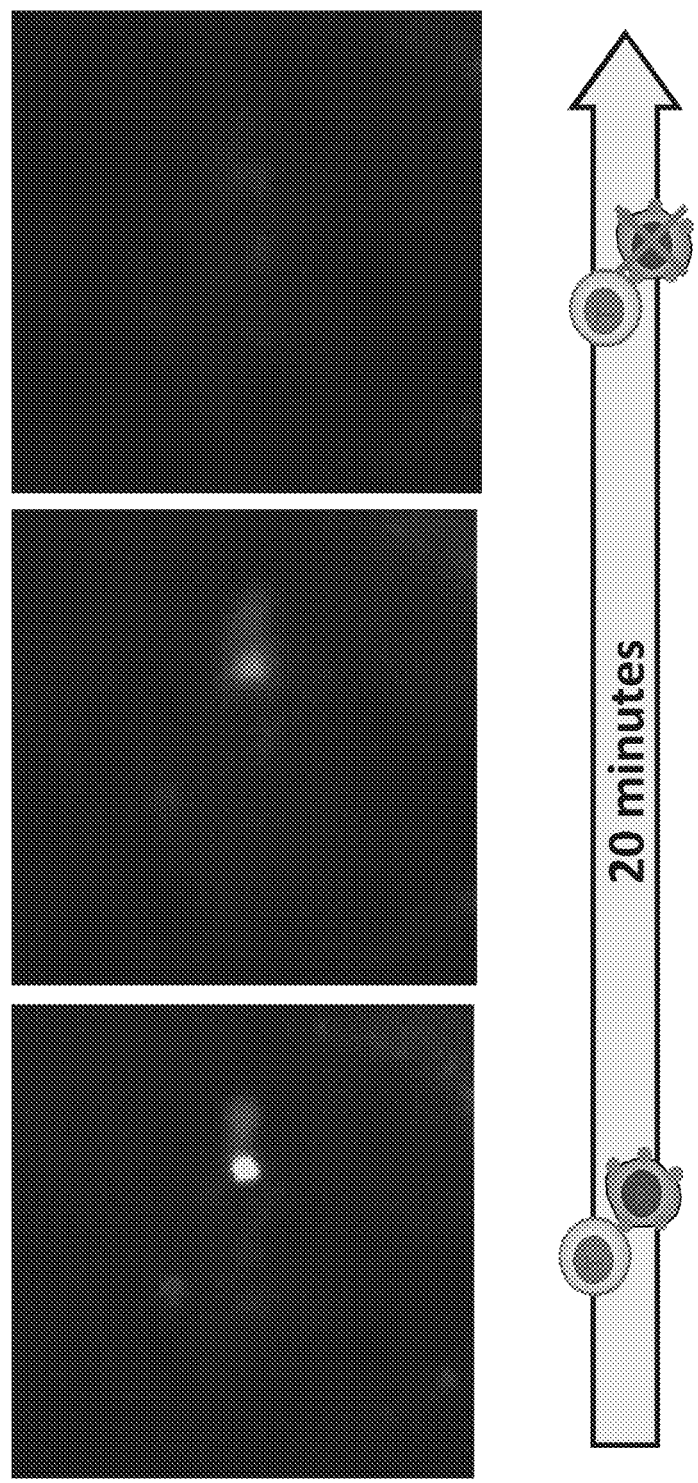
FIG. 7 includes a graph and a series of photographs demonstrating a decrease in biomarker fluorescent signal intensity as a measure of calcein uptake in a living target cell over 20 minutes post exposure of the individual single cells to activated T lymphocytes to induce lysis of the single cell.

Activated CTL cells induced a consistent decrease in fluorescence of the target cells as compared to negative control. Shown in FIG. 7, within 20 minutes the observed fluorescence of the live target cell was diminished and extinguished, demonstrating effective lysis of the target cell induced by the CTL, an effective analysis of specific cell-to-cell induced interaction and measured functional result, within minutes in the inverted open microwell system.

Table 5 reports the fluorescence intensity measured on several LCL targets delivered in inverted open microwells having a diameter of 70 μm. As a control we delivered LCL cells alone. The CTL-LCL interaction was measured in two conditions: without Human Papillomavirus (HPV) infection on target LCL and with HPV infection. In the first case no lysis is expected, while in the second case the CTL cells are expected to recognize the target and lyse the LCL cells. Results reported in the table show that the fluorescence intensity has a strong decrease within 30 minutes for all CTL-LCL couples when the LCL was infected with HPV (cases e-h). In contrast, in only one case (d) an a-specific lysis was obtained, representing the situation of a target cell being recognized by the CTL cell even without HPV infection. In all the other non-infected cases (a-c) only a physiological decrease of fluorescent signal was observed.

TABLE 5

| Case | Cell types | Time (minutes) | Intensity (relative) |
|---|---|---|---|
| a | LCL (control) | 30 | 57.9% |
| b | CTL-LCL (no HPV) | 20 | 59.8% |
| c | CTL-LCL (no HPV) | 20 | 88.6% |
| d | CTL-LCL (no HPV) | 20 | 23.8% |
| e | CTL-LCL 1 | 30 | 2.3% |
| f | CTL-LCL 2 | 20 | 6.2% |
| g | CTL-LCL 3 | 15 | 0.0% |
| h | CTL-LCL 4 | 15 | 4.5% |

Example 4

Controlled Delivery of Particles in Microwells with Active Fluid Flow

Experiments were performed to validate the functionality of the inverted open microwell structures shown, for example in the Figures. Devices were produced, having microwells with a circular diameter of 100 μm, a dielectric with a thickness of 50 μm and 25 μm. The thickness of each electrode was 9 μm. The gap 8 between electrodes 153 and 154 was 50 μm. The microchannel had a height of 150 μm and a width of 350 μm.

Polystyrene microbeads with a diameter of 10 μm were suspended in glycerol (22.5 mM). Glycerol has a density higher than water and is used to reduce the sedimentation speed, thus limiting the adhesion of microbeads to the lower surface of the microchannel. K562 cells were suspended in a 1:9 mixture of PBS and glycerol (300 mM). This buffer has a physiological osmolarity while the conductivity is reduced to about 0.1 S/m.

In two different experiments microbeads and cells were introduced into the microchannel and control electrodes 116, 153, 154, 155, 156, 118 were polarized so as to force (trapping) or prevent (ejecting) particle delivery to the microwells. Except for electrodes tied to ground, all the signals were sinusoids with a frequency of 100 kHz and the same amplitude. The phase shift scheme is reported in Table 6. The functionality of control electrodes was determined by a statistical analysis of the number of particles delivered to microwells for each of the particles and the cells delivered, as a function of the particle speed and the applied voltage.

TABLE 6

| | Electrode | | | | | |
|---|---|---|---|---|---|---|
| Configuration | 116 | 153 | 154 | 155 | 156 | 118 |
| Trapping | (GND) | (GND) | (GND) | 0 | π | π/2 |
| Ejecting | (GND) | π | 0 | 0 | π | π/2 |

When the trapping configuration was active, the number of particles delivered to the microwells increased for higher signal amplitudes and lower fluid speeds. Detailed results are reported in Table 7 and Table 8, where at least 50 samples were considered per each value reported.

When the ejecting configuration was active we found the structure worked properly (i.e. no particles delivered) for peak to peak voltage amplitudes greater than 2V and for any particle speed within the range 15-150 μm/s.

Flow speeds lower than 15 μm/s are typically not used as they result in particle adhesion to the lower surface of the microchannel. The ejecting configuration provided higher stress on cells than the trapping configuration, as demonstrated by calcein release assays performed on the cells flowing through the channel. As a consequence, when working with cells, peak-to-peak voltage amplitude is preferably kept below 10V to limit stresses on the cells and maintain cell viability.

TABLE 7

| Applied peak-peak voltage (V) | Particle and fluid speed (μm/s) | | | | | |
|---|---|---|---|---|---|---|
| | 15 | 20 | 30 | 60 | 100 | 150 |
| 2 | 58% | 50% | 40% | 0% | 0% | 0% |
| 4 | 95% | 95% | 95% | 57% | 0% | 0% |
| 6 | 95% | 95% | 85% | 80% | 50% | 0% |
| 8 | 95% | 95% | 100% | 72% | 0% | 0% |
| 10 | 100% | 100% | 96% | 75% | 10% | 0% |
| 15 | 100% | 100% | 96% | 82% | 30% | 0% |
| 20 | 100% | 100% | 100% | 90% | 30% | 0% |

TABLE 8

| Applied peak-peak voltage (V) | Particle and fluid speed (μm/s) | | | | |
|---|---|---|---|---|---|
| | 15 | 20 | 30 | 60 | 100 |
| 10 | 92% | 87% | 82% | 75% | 30% |
| 15 | 97% | 95% | 95% | 85% | 35% |
| 20 | 95% | 92% | 91% | 93% | 50% |

Example 5

Control of the Environment Outside the Inverted Open Microwell to Reduce Evaporation and Increase Cell Viability The positive effect of controlling the environment surrounding the inverted open microwell was demonstrated by setting up a system where the humidity outside the microwell was brought to its saturation value and by measuring the consistent reduction of the drag force due to evaporation.

The setup used to control the evaporation included a 384-well microtiter plate, where each microwell was filled with 100 uL of fluid, such as water, RPMI, PBS or any buffer suitable for cell culturing stored at a temperature between 4° C. and 10° C. The inverted open microwell array 114 was leaned upon the microtiter in such a way that each well of the microtiter was aligned to an inverted open microwell, creating a closed chamber containing the fluid previously deposited in the microtiter that could evaporate in the closed chamber thus increasing the humidity. The vertical distance between the pool and the meniscus 122 of the inverted open microwell typically ranged from 0.5 mm to 5 mm. After a few minutes the vapor pressure in the chamber reached its saturation value and prevented any further evaporation either from the microtiter and from the inverted open microwell.

To demonstrate the positive effect of the control of the humidity under the microwell in reducing the evaporation in the microwell, a device 101 featuring microwells with the electrode configuration shown in FIG. 2 was used. Electrodes 116 and 120 were tied to ground, while electrode 118 was connected to a sinusoidal signal having a frequency of 100 kHz and variable amplitude.

A suspension of K562 cells maintained at a temperature between 30° C. and 37° C. was inserted in the microchannel and the fluid flow was stopped in order to have a single cell disposed in the microchannel over the microwell entrance. In presence of evaporation, the cell is subjected to a drag force $F_D$ directed downwards and due to the flow of fluid produced by evaporation at the air-fluid interface. In addition, the cell was subjected to the gravity force $F_G$, the buoyancy force $F_B$ and the vertical component of the dielectrophoretic force $F_{DEPy}$ in such a way that:

$$F_B - F_G - F_D = F_{DEPy}.$$

For a relatively high value of the dielectrophoretic force, the cell does remain trapped at the entrance of the microwell and the forces acting on the cell result to be in equilibrium. When the dielectrophoretic force is decrease, the vertical position of the cell decreases and the cell reaches a region where the electric field and the dielectrophoretic force are higher. This behavior is observed until the amplitude of the electric field reaches a critical minimum value. If the amplitude is further decreased, then the cell falls into the microwell as the dielectrophoretic force is not strong enough to counteract the other forces acting on the cell.

The vertical position of the cell of an inverted open microwell surrounded by air was compared with or without humidity control. The reference value for the height was the top side of the top electrode 116. Positive values of the height correspond to particles remaining outside of the microwell in the microchannel, while negative values correspond to particles entering in the microwell. As reported in Table 9, cell height was always higher when the humidity was controlled. This demonstrates that the additional drag force $F_D$ due to evaporation was effectively removed by the presence of the setup that provided controlled humidity under the inverted open microwell.

TABLE 9

| Amplitude (V) | Cell height without humidity control | | Cell height with humidity control | | Theoretical cell height |
|---|---|---|---|---|---|
| | Mean | Standard deviation | Mean | Standard deviation | |
| 0.66 | −28.25 | 0.00 | −6.00 | 5.96 | −5.9 |
| 0.75 | −14.82 | 2.60 | 2.80 | 2.28 | −1.2 |
| 0.85 | −11.36 | 5.01 | 5.20 | 1.92 | 2.4 |
| 0.945 | −7.96 | 7.42 | 7.20 | 1.64 | 4.9 |
| 1.035 | −3.50 | 7.08 | 10.80 | 3.83 | 6.9 |

The control of evaporation is needed to maintain a proper physiological environment for cells trapped on the meniscus at the air-fluid interface. In fact, the presence of evaporation would introduce an increase in the local concentration of salts and other nutrients contained in the medium with a consequent increase in osmolar pressure. After applying the evaporation control we measured cell viability with a standard calcein release assay where cells were stained with Calcein 1 μM and obtained a signal loss of about 8% per hour, which is comparable to the well-known physiological loss, as reported in Neri et al., 2001, *Clin. Diagn. Lab. Immunol.*, vol. 8, no. 6, pp. 1131-1135 "Calcein-Acetyoxymethyl Cytotoxicity Assay: Standardization of a Method Allowing Additional Analyses on Recovered Effector Cells and Supernatants".

The specification includes numerous citations to published references and patent documents, each of which is hereby incorporated by reference in its entirety.

While the invention has been illustrated and preferred embodiments described in the forgoing specification and figures, it is understood that variations and changes can be made to the preferred embodiments without deviating from the scope and spirit of the invention, for example, as embodied in the following claims.

We claim:

1. A method for producing an aggregate of specific particles, comprising:
   a) inserting a first group of particles into a liquid contained in a microchannel of an inverted open microwell system, the system comprising one or more microwells open at an upper end to the microchannel and open at a lower end to a gas outside the lower end of the one or more microwells, wherein the one or more microwells have a depth equal to or greater than a diameter of the one or more microwells;
   b) delivering one or more particles of the first group of particles to the one or more microwells;
   c) depositing the delivered one or more particles to a location on a meniscus formed at an interface between the liquid and the gas at the lower end of the one or more microwells; and
   d) repeating steps a), b) and c) as needed to form an aggregate of specific particles positioned at the meniscus of the one or more microwells;
   wherein the delivered one or more particles descend from the upper end of the one or more microwells to the meniscus at the lower end of the one or more microwells by gravitational force; wherein the inverted one or more microwells are capable of retaining a stable meniscus at the lower open end of the one or more microwells; and wherein the formed aggregate is stably retained on the meniscus, in the absence of an electrical field, while the liquid contained in the microchannel flows through the microchannel.

2. The method of claim 1, wherein the inverted open microwell system further comprises one or more electrodes disposed within each of said one or more microwells, disposed within the microchannel, or a combination thereof, and wherein descent of the delivered one or more particles to the deposit location is driven by:
   a) a combination of gravitational force and one or more electric field generated between electrodes disposed in the one or more microwells; or
   b) a combination of gravitational force and one or more electric field generated between at least one electrode disposed in the one or more microwells and at least one electrode disposed in the upper end of the one or more microwells, and/or in the microchannel.

3. The method of claim 1, wherein the first group of particles include live cells, non-living particles comprising biological molecules, or a combination thereof.

4. The method of claim 1, wherein during at least part of the descent of the delivered one or more particles to the meniscus at the lower end of the one or more microwells, an electric field holds the delivered one or more particles at a central position in a horizontal axis of the one or more microwells as the delivered one or more particles descend along a vertical axis of the one or more microwells, so that the delivered one or more particles that are delivered to an individual microwell of the one or more microwells are in direct contact with each other at the meniscus.

5. The method of claim 1, further comprising the step of controlling entry of one or more particles of the first group of particles into the one or more microwells by:
   a) controlling liquid flow in the microchannel at a sufficiently low speed to permit the one or more particles of the first group of particles to enter the one or more microwells;
   b) activating a pair of electrodes disposed at the upper end of the one or more microwells to control entry of the one or more particles of the first group of particles into the one or more microwells; or
   c) both controlling liquid flow as in a) and activating a pair of electrodes as in b).

6. The method of claim 1, further comprising one or more of the following steps:
   a) analyzing one or more of the deposited and delivered one or more particles for a detectable functional response, the detectable functional response selected from:
      i) ligand/receptor binding;
      ii) target cell lysis;
      iii) inhibition of cell growth;
      iv) stimulation of or inhibition of apoptosis;
      v) production of a biomarker
      vi) binding to a specific antigen;
      vii) lysis of a target cell;
      viii) production of an antigen-specific antibody;
      ix) therapeutic drug effect;
      x) apoptosis of a target cell;
      xi) inhibition of cell death;
      xii) production of a specific biological molecule;
      xiii) cell differentiation; and
      xiv) a cell signaling event in a target cell;
   b) viewing one or more of the deposited and delivered one or more particles with a microscope, wherein the deposited and delivered one or more particles is one or more cells; and
   c) recovering the deposited and delivered one or more particles from the one or more microwells.

7. The method of claim 1, wherein the aggregate of specific particles comprises two or more cells that form a functional aggregate, the two or more cells in direct contact with each other, and further comprising the step of analyzing the functional aggregate to detect a functional response, the detectable functional response selected from:
   a) ligand/receptor binding;
   b) target cell lysis;
   c) inhibition of cell growth;
   d) stimulation of or inhibition of apoptosis;
   e) production of a biomarker
   f) binding to a specific antigen;
   g) lysis of a target cell;
   h) production of an antigen-specific antibody;
   i) therapeutic drug effect;
   j) apoptosis of a target cell;
   k) inhibition of cell death;
   l) production of a specific biological molecule;
   m) cell differentiation; and
   n) a cell signaling event in a target cell.

8. The method of claim 1, further comprising one or more of the following steps:
   a) viewing one or more of the deposited and delivered one or more particles of the aggregate of specific particles stably retained at the meniscus with a microscope positioned below the lower open end of the one or more microwells or above the microchannel;
   b) recovering the aggregate of specific particles from the one or more microwells by applying a pressure pulse in the microchannel resulting in transfer of the contents of the one or more microwells to a substrate disposed below the lower end of the one or more microwells; and
   c) recovering the contents of the one or more microwells directly onto the substrate disposed beneath the lower end of the one or more microwells.

9. The method of claim 1, wherein the one or more microwells of the inverted open microwell system comprises a plurality of inverted open microwells.

10. The method of claim 9, wherein the plurality of inverted open microwells comprises an array of inverted open microwells open to the microchannel, and further comprising the step of transferring the contents of the array of inverted open microwells in parallel to a multi-well substrate.

11. The method of claim 9, wherein the plurality of inverted open microwells comprises an array of inverted open microwells open to an atmosphere outside the system that is controlled for composition, humidity, temperature, pressure, and sterility.

12. The method of claim 1, wherein delivering the one or more particles comprises:
   a) applying controlled potential to opposing electrodes disposed at opposing walls of the microchannel along a vertical axis to create a dielectrophoretic force sufficient to cause a particle in the microchannel to move toward the one or more microwells; and
   b) applying controlled potential to opposing electrodes disposed at opposing walls of the one or more microwells and/or to one or more electrodes disposed at a top side of the microchannel along a horizontal axis to create a dielectrophoretic force sufficient to cause one or more particles of the delivered one or more particles to move into the one or more microwells.

13. The method of claim 12, further comprising a step of detecting an absence of one or more particles in the one or more microwells using a sensor and responding to the detected absence by causing electrodes disposed at opposing walls and toward the upper end of the one or more microwells and/or electrodes disposed at a top side of the microchannel along a horizontal axis to generate a dielectrophoretic force to move one or more particles of the delivered one or more particles into the one or more microwells, wherein the detecting step occurs before, during, or after the delivery of the one or more particles of the first group of particles from the microchannel to the one or more microwells.

14. The method of claim 1, wherein delivering the one or more particles comprises:
   a) applying controlled potential to opposing electrodes disposed at opposing walls of the microchannel along a vertical axis to create a dielectrophoretic force sufficient to cause a particle in the microchannel to move away from the one or more microwells; and/or
   b) applying controlled potential to opposing electrodes disposed at opposing walls of the one or more microwells and/or to one or more electrodes disposed at a top side of the microchannel along a horizontal axis to create a dielectrophoretic force sufficient to cause one or more particles of the delivered one or more particles to be repelled from the one or more microwells.

15. The method of claim 1, further comprising a step of detecting an absence of one or more particles in the one or more microwells using a sensor and responding to the detected absence by causing electrodes disposed at opposing walls and toward the upper end of the one or more microwells and/or electrodes disposed at a top side of the microchannel along a horizontal axis to generate a dielectrophoretic force to deliver one or more particles of the delivered one or more particles into the one or more microwells.

16. The method of claim 1, further comprising the steps of detecting passage of one or more particles of the first group of particles in the microchannel using an optical or electrical sensor positioned along the microchannel; and responding to the detection of the one or more particles of the first group of particles by causing electrodes disposed at opposing walls and toward the upper end of the one or more microwells to generate a dielectrophoretic force to deliver the one or more particles of the first group of particles into the one or more microwells or to repel the one or more particles of the first group of particles away from the one or more microwells.

17. The method of claim 16, wherein opposing electrodes disposed at opposing walls of the microchannel along a vertical axis create a dielectrophoretic force sufficient to cause the one or more particles of the first group of particles in the microchannel to align along an axis where the detection is performed by the optical or electrical sensor.

18. The method of claim 1, wherein a plurality of paired electrodes are disposed in the microchannel, and wherein the step of delivering the one or more particles of the first group of particles from the microchannel to the one or more microwells comprises:
   a) applying a potential to one or more of the electrode pairs to generate one or more electric fields sufficient to cause one or more particles of the first group of particles to move in the microchannel toward the one or more microwells;
   b) trapping the one or more particles of the first group of particles in the microchannel at a position above a microwell of the one or more microwells;
   c) applying a potential to one or more electrodes in the microchannel and/or in the microwell of the one or more microwells to cause the particle to enter the microwell of the one or more microwells; and
   d) permitting the particle to descend along a vertical axis of the microwell of the one or more microwells by gravitational force and depositing the particle at the location on the meniscus at a lower end of the microwell of the one or more microwells.

19. The method of claim 1, further comprising the steps of:
   a) providing one or more reactants to the delivered one or more particles deposited at the location on the meniscus by adding the one or more reactants to the microchannel that is in liquid communication with the one or more microwells; and
   b) correlating a change in the deposited and delivered one or more particles or the one or more reactants with a specific functional activity possessed by the deposited and delivered one or more particles or the one or more reactants.

20. The method of claim 1, wherein the delivered and deposited one or more particles is selected from one or more of:
   a) a target particle comprising a specific ligand;
   b) a target cell comprising a specific ligand;
   c) a cytotoxic and/or cytolytic target cell;
   d) a diseased cell;
   e) an immune cell;
   f) a cancer cell;
   g) an HIV infected cell;
   h) a transgenic cell;
   i) an immortalized cell; and
   j) a B-cell.

21. The method of claim 8, wherein the contents of individual microwells of the one or more microwells remain separate upon transfer.

22. The method of claim 10, wherein the contents of each individual microwell of the array of inverted open microwells is transferred to a separate well of the multi-well substrate.

* * * * *